United States Patent
Yanai et al.

(10) Patent No.: US 9,567,617 B2
(45) Date of Patent: Feb. 14, 2017

(54) MUTANT XYLANASE, MANUFACTURING METHOD AND USE THEREFOR, AND METHOD FOR MANUFACTURING SACCHARIFIED LIGNOCELLULOSE

(71) Applicants: Mitsui Chemicals, Inc., Tokyo (JP); Meiji Seika Pharma Co., Ltd., Chuo-ku, Tokyo (JP)

(72) Inventors: Hisaaki Yanai, Mobara (JP); Hiroki Tamai, Ichihara (JP); Masami Osabe, Chiba (JP); Fumikazu Yokoyama, Yokohama (JP); Kaoru Okakura, Odawara (JP); Atsushi Inoue, Odawara (JP)

(73) Assignees: MITSUI CHEMICALS, INC., Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/042,395

(22) Filed: Feb. 12, 2016

(65) Prior Publication Data
US 2016/0168555 A1 Jun. 16, 2016

Related U.S. Application Data

(62) Division of application No. 14/360,514, filed as application No. PCT/JP2012/080387 on Nov. 22, 2012.

(30) Foreign Application Priority Data

Nov. 25, 2011 (JP) ................................. 2011-257389
Apr. 24, 2012 (JP) ................................. 2012-099096

(51) Int. Cl.
| | |
|---|---|
| C12N 9/24 | (2006.01) |
| C12N 9/42 | (2006.01) |
| C07H 21/04 | (2006.01) |
| C12N 15/64 | (2006.01) |
| C12P 19/02 | (2006.01) |
| C12P 19/14 | (2006.01) |
| C11D 3/386 | (2006.01) |
| A21D 8/04 | (2006.01) |
| C13K 1/02 | (2006.01) |
| C13K 13/00 | (2006.01) |

(52) U.S. Cl.
CPC ............. *C12P 19/02* (2013.01); *A21D 8/042* (2013.01); *A23K 20/189* (2016.05); *C11D 3/38636* (2013.01); *C12N 9/248* (2013.01); *C12N 9/2482* (2013.01); *C12P 19/14* (2013.01); *C12Y 302/01004* (2013.01); *C13K 1/02* (2013.01); *C13K 13/002* (2013.01); *C12Y 302/01008* (2013.01); *C12Y 302/01021* (2013.01); *Y02P 20/52* (2015.11)

(58) Field of Classification Search
CPC ........ C12N 9/248; C12N 9/2482; C12P 19/14; C12P 19/02; C12Y 302/01008; C13K 13/002
USPC .... 435/200, 252.31, 252.33, 320.1; 536/23.2
See application file for complete search history.

(56) References Cited

U.S. PATENT DOCUMENTS

| | | | |
|---|---|---|---|
| 5,658,765 | A | 8/1997 | Noguchi et al. |
| 6,682,923 | B1 | 1/2004 | Bentzien et al. |
| 2009/0148923 | A1 | 6/2009 | Sung |

FOREIGN PATENT DOCUMENTS

| | | |
|---|---|---|
| CN | 1177639 A | 4/1998 |
| CN | 101429516 | 5/2009 |
| EP | 2 505 657 A1 | 10/2012 |
| JP | 10-215866 | 8/1998 |
| JP | 2000-166485 A | 6/2000 |
| JP | 2001-017180 A | 1/2001 |
| JP | 2004-121257 A | 4/2004 |
| JP | 2006-087319 A | 4/2006 |
| JP | 2007-054050 A | 3/2007 |
| JP | 2011-045277 A | 3/2011 |
| JP | 2012-010638 A | 1/2012 |
| WO | WO-00/29587 A1 | 5/2000 |
| WO | WO-01/27252 A1 | 4/2001 |
| WO | WO-01/92487 A2 | 12/2001 |
| WO | WO-03/046169 A2 | 6/2003 |
| WO | WO-2005/108565 A2 | 11/2005 |

(Continued)

OTHER PUBLICATIONS

Chinese Office Action dated Feb. 28, 2015 issued for Chinese Patent Application No. 201280057199.0.

(Continued)

*Primary Examiner* — Robert Mondesi
*Assistant Examiner* — MD. Younus Meah
(74) *Attorney, Agent, or Firm* — Foley & Lardner LLP

(57) ABSTRACT

What is aimed at is provision of an inexpensive and efficient saccharification method for lignocellulose using a thermostable xylanase and provision of a mutant xylanase that has a substitute amino acid residue, and that exhibits stable activity even under severe conditions in which enzymes easily inactivate, and that provides an initial rate of reaction not significantly reduced as compared to a wild-type xylanase corresponding to the mutant xylanase. Provided is a method of producing a saccharified product of lignocellulose, including contacting a lignocellulosic raw material with a thermostable xylanase, and a mutant xylanase that provides an initial rate of reaction that is at least 70% of that provided by a wild-type xylanase corresponding thereto, that has a xylanase activity after heat treatment at 50° C. for 24 hours that is at least 50% of its xylanase activity before the heat treatment, and that has a substitute amino acid residue.

8 Claims, No Drawings

(56) References Cited

FOREIGN PATENT DOCUMENTS

| WO | WO-2007/115391 A1 | 10/2007 |
|----|-------------------|---------|
| WO | WO-2007/115407 A1 | 10/2007 |
| WO | WO-2011/065449 A1 | 6/2011 |
| WO | WO-2011/125056 A1 | 10/2011 |

OTHER PUBLICATIONS

Database DDBJ/EMBL/GenBank [online], Accession No. CAD33900, <http://www.ncbi.nlm.nih.gov/protein/26986133>, Definition: endo-1,4-xylanase B [Penicilliom funiculosum] Uploaded Nov. 14, 2006; retrieved on Dec. 5, 2012. 1 page.

Devos et al., "Practical Limits of Function Prediction," Proteins: Structure, Function, and Genetics 41, pp. 98-107 (2000).

European Search Report corresponding to Application No. 12 851 111.0, dated Jul. 3, 2015.

Extended European Search Report issued in European Application No. 12851111.0 dated Oct. 26, 2015.

International Search Report dated Dec. 18, 2012 issued in International Application No. PCT/JP2012/080387.

Kisselev, "Polypeptide Release Factors in Prokaryotes and Eukaryotes: Same Function, Different Structure," Structure 10, pp. 8-9 (Jan. 2002).

Non-Final Office Action for U.S. Appl. No. 14/360,514, mailed Jul. 13, 2015.

Notice of Allowance for U.S. Appl. No. 14/360,514, mailed Dec. 7, 2015.

Whisstock et al., "Prediction of protein function from protein sequence and structure," Quarterly Reviews of Biophysics 36(3), pp. 307-340 (2003).

Witkowski et al., "Conversion of a β-Ketoacyl Synthase to a Malonyl Decarboxylase by Replacement of the Active-Site Cysteine with Glutamine," Biochemistry 38, pp. 11643-11650 (1999).

MUTANT XYLANASE, MANUFACTURING METHOD AND USE THEREFOR, AND METHOD FOR MANUFACTURING SACCHARIFIED LIGNOCELLULOSE

CROSS-REFERENCE TO RELATED PATENT APPLICATIONS

The present application is a divisional of U.S. patent application Ser. No. 14/360,514, filed May 23, 2014, U.S. Pat. No. 9,394,554 which is the National Phase of PCT/JP2012/080387, filed Nov. 22, 2012, which claims priority to Japanese Application No. 2011-257389, filed Nov. 25, 2011 and Japanese Application No. 2012-099096, filed Apr. 24, 2012 the disclosures of which are hereby incorporated by reference in their entirety.

TECHNICAL FIELD

The present invention relates to a method of efficiently producing a saccharified product from a lignocellulosic raw material. The invention also relates to a mutant xylanase, a method of producing the mutant xylanase, and uses of the mutant xylanase.

BACKGROUND ART

Xylanase is an enzyme that randomly hydrolyzes β-1,4 bonds of xylan, which is a component of plant cell walls. The enzyme is expected to be used in a wide range of applications, such as a) saccharification of lignocellulosic raw materials, b) pulp bleaching, c) animal feed additives, d) detergent aids, and e) bread-making modifiers.

With regard to a) saccharification of lignocellulosic raw materials, a method for saccharification of a lignocellulosic raw material is known in which a monosaccharide serving as a fermentation substrate is produced from a lignocellulosic raw material using an enzyme. However, the expensiveness of enzymes such as cellulases and hemicellulases (xylanase or the like) that can be used for this saccharification method hinders practical use of this saccharification method. Addressing this problem, reutilization of enzymes used in the saccharification method has been proposed as a means effective for the reduction of the cost of the saccharification method (see, for example, Japanese Patent Application Laid-Open (JP-A) No. 2006-87319 (Patent Document 1), International Publication WO2011/065449 pamphlet (Patent Document 10) and WO2011/125056 pamphlet (Patent Document 11)).

Xylanase is an enzyme that breaks down hemicellulose (of which the main component is β-1,4-xylan), which is one of the main components of a lignocellulosic raw material. Therefore, xylanase is one of important enzymes in a method for saccharifying a lignocellulosic raw material. However, xylanase is known to have low stability.

Meanwhile, saccharification of a lignocellulosic raw material requires treatment in an acidic region of from pH 4.0 to pH 6.0 at a high temperature of from 40° C. to 60° C. for a few days. Thus, the low stability of xylanase is a hindrance to the reutilization of this enzyme.

A heat-resistant xylanase mutant derived from *Trichoderma reesei* (hereinafter abbreviated to "*T. reesei*") (see, for example, WO 2007/115391 pamphlet (Patent Document 2) and WO 2007/115407 pamphlet (Patent Document 3)) exhibited a residual activity of 80% or higher even after heat treatment at from 50° C. to 70° C. for 30 minutes.

A *Bacillus*-derived heat-resistant xylanase (see, for example, JP-A No. 2004-121257 (Patent Document 4)) is also known to exhibit a residual activity of 90% or higher after heat treatment at 70° C. for 30 minutes.

In regard to b) pulp bleaching, it is known that the amount of bleaching agent to be used can be decreased by using xylanase in a pulp bleaching process.

In general, pulp bleaching in paper-making industry consists of a first stage which is a delignification treatment process (from pH 10 to 12, 80° C.) of removing lignin from pulp using an enzyme, and a second stage which is a bleaching process. The reason for performing the bleaching process in the second stage as described above is that about a few percent of lignin remains as a coloring component in the pulp even after the delignification treatment using an enzyme. Addition of a process of allowing xylanase to work, in addition to the delignification treatment process and the bleaching process, enables the breakage of hemicellulose chains bound to lignin and cellulose. As a result of this, lignin can be effectively removed, and it is expected that an effect in terms of decreasing the amount of bleaching agent to be used in the bleaching process can be obtained.

In order to efficiently perform the process of allowing xylanase to work, it is necessary to use a xylanase having properties such that the xylanase can tolerate treatment at about pH 10 and from 70° C. to 80° C. carried out for a few hours.

A heat-resistant xylanase mutant derived from *T. reesei* (see, for example, Patent Documents 2 and 3, and WO 2001/92487 (Patent Document 5) and WO 2003/046169 (Patent Document 6)) has an optimum reaction temperature of about 70° C. and an optimum reaction pH of from 7 to 8, demonstrating the possibility that the heat-resistant mutant xylanase can be used in a pulp bleaching process.

With regard to c) animal feed additives, animal feed is rich in plant fibers, and plant cell walls in the animal feed can be decomposed by adding xylanase. Therefore, the efficiency of absorption of plant nutrition by animals can be improved.

In cases in which animal feed is to be pelletized using xylanase, the xylanase is required to have stability with which the xylanase can tolerate treatment at from about 70° C. to about 90° C. for about 10 minutes. In addition, in order for the xylanase to work in the digestive organs of animals, the xylanase needs to exhibit high activity in an environment at about 40° C. and about pH 4.8.

Many of xylanases derived from filamentous fungi such as the genus *Trichoderma* and the genus *Acremonium* have an optimum pH of from 3 to 5 and an operable temperature range around 40° C.

The heat-resistant xylanase mutants described in Patent Document 2 Patent Document 3, WO 2001/27252 (Patent Document 7), and WO 2005/108565 (Patent Document 8) include mutants having an optimum pH of from about 5 to about 5.5.

d) Detergent Aid: The use of xylanase as a detergent aid can remove fluff on clothes.

Since recent drum-type washing machines are designed to save water, fine fluffing tends to occur as the number of times of washing increases. When the fluffing has occurred, re-soiling of clothes tends to occur.

The fluff can be removed by using xylanase as a detergent aid, and, therefore, re-soiling can also be prevented. Moreover, since the main components of stains attaching to clothes and derived from vegetables or fruits are cell walls which are derived from the vegetables or fruits and to which colorants are attached, effective washing can be carried out using xylanase in washing even in cases in which a water-saving-type drum-type washing machine is used.

In cases in which xylanase is to be used as a detergent aid, it is necessary to use a xylanase having alkali resistance and surfactant resistance. In addition, in cases in which xylanase is used in laundry cleaning, it is necessary to use a xylanase that stably works in a high temperature range of from 50° C. to 70° C.

A *T. reesei*-derived xylanase mutant having heat resistance and alkali resistance (for examples, see Patent Document 2, Patent Document 3, Patent Document 5, and Patent Document 6) has properties including an optimum temperature of from 62° C. to 75° C. and an optimum pH of from pH 7 to pH 8.

The xylanase mutant described in Patent Document 8 has an optimum pH of pH 5, which is at the acidic side. However, this mutant xylanase has an optimum temperature of 70° C., and maintains 100% activity at 60° C. and from pH 8 to pH 9 for at least 10 minutes.

Each of the heat-resistant and alkali-resistant xylanases derived from the genus *Bacillus* (see, for example, Patent Document 4 and JP-A No. 2007-54050 (Patent Document 9)) has properties including an optimum temperature range of from 50° C. to 70° C. and an optimum pH of from 7 to 8, and maintain 100%-activity at pH 9 and from 4° C. to 5° C. for a length of time of from 1 to 2 days.

In regard to e) bread-making modifiers, the quality of bread production can be improved by using xylanase as a bread-making modifier.

Xylanase has properties capable of decomposing the hemicellulose component of flour. Due to the decomposition of the hemicellulose component by xylanase, moisture bound to this component is released into dough, thereby changing the properties of the dough. As a result, the particle structure and the loaf volume of the produced bread are improved, leading to favorable quality preservation of the produced bread.

When making dough, large physical impact and pressure load are applied during a process of stirring and kneading ingredients, and a fermentation process requires a length of time of from 1 to 2 hours at a temperature of from 35° C. to 40° C.

SUMMARY OF INVENTION

Problem to be Solved by Invention

However, there is still room for improvement in the reutilization of the saccharification enzyme described in (a) saccharification of lignocellulosic raw material, from the viewpoints of the cost of sugar production and the effective utilization of lignocellulosic resources.

In the reutilization of the saccharification enzyme described in Patent Document 1, it is demonstrated that the binding of the enzyme to a lignocellulosic residue causes reduction in the saccharification activity thereof. For this reason, the addition amounts of the enzyme and the substrate are significantly limited.

In particular, the working examples of Patent Document 1 describes that the amount of the enzyme is an amount capable of decomposing 96% or more of lignocellulose in 12 hours, indicating that feeding of a large amount of the enzyme is necessary. Thus, from an economical viewpoint, enzyme reutilization over a long period of time is necessary.

In addition, the concentration of lignocellulose as a substrate is as low as about 1%, and the concentration of produced sugar is also low. Therefore, for the utilization of the sugar in an ethanol fermentation process and the like, investment for facilities for addressing the efficiency per volume of the saccharification tank, the concentrating before ethanol fermentative production, and the like, is necessary. Thus, this method can hardly be regarded as an industrial method from the economical viewpoint.

In the saccharification of lignocellulose containing hemicellulose, it is thought that an enzyme capable of decomposing lignocellulose at high concentration and tolerating reutilization over a long period of time is needed. Therefore, the lowness of the stability of xylanase is a problem, as described above.

In Patent Document 10, it is described that the activity of enzymes such as cellulase and hemicellulase is maintained even after adsorption on residues. Patent Document 10 also describes a method whereby a saccharification enzyme is recovered by being adsorbed on lignocellulose after reaction and reutilized in a next saccharification reaction.

However, in Patent Document 10, lignocellulose that will be used as a saccharification raw material is heated, in advance, under acidic conditions, whereby hemicellulose in the lignocellulose is decomposed. Therefore, heating costs are incurred, and installation of equipment such as a pressure vessel having resistance to acid is needed. Accordingly, this method is not favorable from the economical viewpoint.

In view of these, decomposition of hemicellulose using xylanase is desired. However, since the saccharification reaction is carried out for a long time, the lowness of the stability of xylanase is a problem, similar to the above.

Patent Document 11 describes that, by increasing the amount of saccharification enzyme to be used in an initial reaction, the amount of enzyme to be additionally supplied, which corresponds to the activity lost at the time of reutilizing the enzyme, can be decreased, and the overall costs for the enzyme can be decreased.

However, in fact, an amount of the enzyme additionally supplied is as large as ⅓ of the amount of the initially-supplied enzyme, and, therefore, this method is not favorable from the economical viewpoint. In addition, it is described, in working examples provided in Patent Document 11, that reaction residues are disposed of. The loss of the enzyme adsorbed on the residues is a major factor that makes it impossible to decrease the amount of the enzyme to be additionally supplied.

Furthermore, working examples provided in Patent Document 11 describe only the use of cellulose included in lignocellulose, namely the use of glucose. The wheat straw used in working examples provided in Patent Document 11, which has been subjected to pretreatment, contains hemicellulose and the like in an amount of 35% or more. From the viewpoints of effective use of lignocellulose resources and economy, it is necessary to use, as a monosaccharide, xylose contained in the hemicellulose. In this case, however, the lowness of the stability of xylanase is a problem in a situation in which the enzyme is reutilized after long hours of reaction that is expected to include processes from saccharification to ethanol fermentation.

Solutions to these may include utilization of a thermostable xylanase prepared by improving an existing xylanase and utilization of a heat-resistant xylanase derived from a heat-resistant bacterium. However, until now, there has been no report about long-term enzyme utilization using these xylanases.

It is uncertain whether or not the *T. reesei*-derived heat-resistant xylanase mutants disclosed in Patent Document 2 and Patent Document 3 mentioned in (a) saccharification of lignocellulosic raw material satisfy conditions required for the saccharification of a lignocellulosic raw material (long-term use in an acidic region at high temperatures).

Further, in regard to the heat-resistant xylanase that is derived from the genus *Bacillus* and that is described in Patent Document 4 mentioned in (a), the results of residual activity thereof upon heat treatment at pH 7.2, which is close to neutral pH, are disclosed. Therefore, the activity of the heat-resistant xylanase is likely to decrease when the heat-resistant xylanase has been used under acidic conditions for a few days in order to perform the saccharification of lignocellulose.

In Patent Document 2, Patent Document 3, Patent Document 5, and Patent Document 6, which are directed to *T. reesei*-derived heat-resistant xylanase mutants and mentioned in (b) pulp bleaching, data about the residual activity of the *T. reesei*-derived heat-resistant xylanases after the *T. reesei*-derived heat-resistant xylanases are treated at pH 5 and from 60° C. to 80° C. for 30 minutes. However, the stability of the *T. reesei*-derived heat-resistant xylanases under conditions simulating pulp bleaching (at pH 10 and from 70° C. to 80° C. for a few hours) is not demonstrated.

The xylanases derived from filamentous fungi such as the genus *Trichoderma* and the genus *Acremonium* mentioned in (c) animal feed additives do not have thermal stability that can tolerate pelleting.

Further, among the heat-resistant xylanase mutants disclosed in Patent Document 2, Patent Document 3, Patent Document 7, and Patent Document 8 mentioned in (c), mutants having an optimum pH of from about 5 to about 5.5 are included. However, all of the mutants undergo significant thermal inactivation in a high temperature range of 60° C. or higher, and, therefore, these mutants cannot be used as animal feed additives.

In regard to the *T. reesei*-derived heat-resistant and alkali-resistant xylanase mutants disclosed in Patent Document 2, Patent Document 3, Patent Document 5, and Patent Document 6 mentioned in (d) Detergent Aid, there is no information about the stability of the alkali-resistant xylanase mutants in a basic region over a length of time generally required for washing (from 1 to 2 hours). It is thus unclear whether or not these mutant xylanases can be used as detergent aids.

Similar to the above, it is unclear whether or not the xylanase mutant disclosed in Patent Document 8 and the heat-resistant and alkali-resistant xylanases derived from the genus *Bacillus* and disclosed in Patent Document 4 and Patent Document 9, which are mentioned in (d), can tolerate the use as a detergent aid in laundry cleaning.

It is not clarified whether or not the *T. reesei*-derived heat-resistant xylanase mutants disclosed in Patent Document 2, Patent Document 3, Patent Document 5, and Patent Document 6, which are mentioned in (e) bread-making modifier, can tolerate large physical impact and pressure load applied during bread making.

Further, bread-making processes include a fermentation process performed at from 35° C. to 40° C. for 1 to 2 hours. Thus, compatibility with this process is also required.

As described above, the range of uses in which xylanase can be used is wide. Therefore, conditions required for xylanase vary widely. Examples thereof include severe conditions in which enzymes easily inactivate, such as a condition involving a pH of from 4 to 10, a temperature of from 40° C. to 80° C., and a usage time of several days.

In order to address these various needs, many types of mutant xylanases and novel xylanases have been reported.

However, xylanases that can work with sufficient stability under severe conditions in which enzymes easily inactivate have not been found.

Mutant xylanases obtained in order to improve heat resistance have a problem in that the initial rate of reaction largely decreases. It is presumed that the reason therefor is a decrease in the structural flexibility of the entire protein caused by mutations or the like of the amino acid sequence that has been introduced in order to improve heat resistance.

In such circumstances, development of a xylanase which exhibits stable activity for a predetermined period of time under severe conditions in which enzymes easily inactivate such as an acidic region (from pH 4 to 6), a basic region (from pH 8 to 10), or a high temperature range (from 40° C. to 80° C.), and with which the initial rate of reaction is not significantly reduced as compared to a wild-type xylanase corresponding thereto.

The present invention aims to provide an inexpensive and efficient saccharification method for lignocellulose using a thermostable xylanase. The invention also aims to provide a mutant xylanase that has a substitute amino acid residue, and that exhibits stable activity even under severe conditions in which enzymes easily inactivate, and that provides an initial rate of reaction not significantly reduced as compared to a wild-type xylanase corresponding to the mutant xylanase. The invention also aims to provide a production method capable of producing the mutant xylanase at low cost, as well as provide various uses of the mutant xylanase.

Means for Solving Problem

The present invention includes the following:
[1] A method of producing a saccharified product of lignocellulose, the method including contacting a lignocellulosic raw material with a thermostable xylanase.
[2] The method of producing a saccharified product according to [1], wherein the lignocellulosic raw material is pulp.
[3] A method of producing a saccharified product, the method including:
recovering the thermostable xylanase from a saccharification reaction solution containing the saccharified product of lignocellulose obtained by the method of producing a saccharified product according to [1] or [2]; and
contacting the recovered thermostable xylanase with a lignocellulosic raw material, to produce a saccharified product.
[4] The method of producing a saccharified product according to [3], wherein the saccharification reaction solution is subjected to solid-liquid separation using centrifugation or a microfiltration membrane, and the separated liquid is ultrafiltered using an ultrafiltration membrane to separate and recover the saccharified product of lignocellulose and the thermostable xylanase.
[5] The method of producing a saccharified product according to [4], wherein the method includes contacting a solid obtained by the solid-liquid separation using centrifugation or a microfiltration membrane and the thermostable xylanase recovered using the ultrafiltration membrane with a lignocellulosic raw material, to produce a saccharified product.
[6] The method of producing a saccharified product according to any one of [1] to [5], wherein the thermostable xylanase is a mutant xylanase that provides an initial rate of reaction that is at least 70% of that provided by a wild-type xylanase corresponding thereto, that has a xylanase activity after heat treatment at 50° C. for 24 hours that is at least 50% of its xylanase activity before the heat treatment, and that has a substitute amino acid residue.

[7] The method of producing a saccharified product according to [6], wherein the mutant xylanase is a mutant xylanase including at least the following substitute amino acid residues in an amino acid sequence represented by SEQ ID NO: 1 in the Sequence Listing:
  a leucine residue substituted for an asparagine residue at position 29;
  an arginine residue substituted for a lysine residue at position 58;
  an amino acid residue, other than a tyrosine residue, substituted for a tyrosine residue at position 27; and
  an amino acid residue, other than an asparagine residue, substituted for an asparagine residue at position 44.

[8] The method of producing a saccharified product according to [7], wherein, in the mutant xylanase used in the producing of a saccharified product, the amino acid residue, other than a tyrosine residue, substituted for the tyrosine residue at position 27 is a phenylalanine residue, and the amino acid residue, other than an asparagine residue, substituted for an asparagine residue at position 44 is a serine residue.

[9] The method of producing a saccharified product according to [6], wherein the mutant xylanase is a mutant xylanase in which at least an amino acid residue at position 154 in the amino acid sequence represented by SEQ ID NO: 2 in the Sequence Listing is substituted with another amino acid residue.

[10] The method of producing a saccharified product according to [9], wherein the mutant xylanase used in the producing of a saccharified product includes at least the following substitute amino acid residues:
  an aspartic acid residue substituted for an asparagine residue at position 33;
  an arginine residue substituted for a glycine residue at position 36;
  a serine residue substituted for a threonine residue at position 90;
  an arginine residue substituted for a glutamine residue at position 132;
  a methionine residue substituted for a leucine residue at position 154;
  a threonine residue substituted for a serine residue at position 174;
  a histidine residue substituted for a proline residue at position 195;
  an asparagine residue substituted for a serine residue at position 197; and
  a glutamic acid residue substituted for a glycine residue at position 217.

[11] The method of producing a saccharified product according to [9], wherein the mutant xylanase used in the producing of a saccharified product includes at least the following substitute amino acid residues:
  a valine residue substituted for an isoleucine residue at position 30;
  an aspartic acid residue substituted for an asparagine residue at position 33;
  an arginine residue substituted for a glycine residue at position 36; and
  a methionine residue substituted for a leucine residue at position 154.

[12] The method of producing a saccharified product according to [9], wherein the mutant xylanase used in the producing of a saccharified product includes at least the following substitute amino acid residues:
  a valine residue substituted for an isoleucine residue at position 30;
  a threonine residue substituted for a serine residue at position 59;
  a methionine residue substituted for a leucine residue at position 154;
  a histidine residue substituted for a tyrosine residue at position 239; and
  a serine residue substituted for a cysteine residue at position 242.

[13] A mutant xylanase including at least the following substitute amino acid residues in an amino acid sequence represented by SEQ ID NO: 1 in the Sequence Listing:
  a leucine residue substituted for an asparagine residue at position 29;
  an arginine residue substituted for a lysine residue at position 58;
  an amino acid residue, other than a tyrosine residue, substituted for a tyrosine residue at position 27; and
  an amino acid residue, other than an asparagine residue, substituted for an asparagine residue at position 44.

[14] The mutant xylanase according to [13], wherein the amino acid residue, other than a tyrosine residue, substituted for the tyrosine residue at position 27 in the amino acid sequence represented by SEQ ID NO: 1 in the Sequence Listing is a phenylalanine residue, and the amino acid residue, other than an asparagine residue, substituted for an asparagine residue at position 44 in the amino acid sequence represented by SEQ ID NO: 1 in the Sequence Listing is a serine residue.

[15] A mutant xylanase including substitution of at least a leucine residue at position 154 with another amino acid residue in the amino acid sequence represented by SEQ ID NO: 2 in the Sequence Listing.

[16] The mutant xylanase according to [15], wherein the mutant xylanase includes at least the following substitute amino acid residues in the amino acid sequence represented by SEQ ID NO: 2 in the Sequence Listing:
  an aspartic acid residue substituted for an asparagine residue at position 33;
  an arginine residue substituted for a glycine residue at position 36;
  a serine residue substituted for a threonine residue at position 90;
  an arginine residue substituted for a glutamine residue at position 132;
  a methionine residue substituted for the leucine residue at position 154;
  a threonine residue substituted for a serine residue at position 174;
  a histidine residue substituted for a proline residue at position 195;
  an asparagine residue substituted for a serine residue at position 197; and
  a glutamic acid residue substituted for a glycine residue at position 217.

[17] The mutant xylanase according to [15], wherein the mutant xylanase includes at least the following substitute amino acid residues in the amino acid sequence represented by SEQ ID NO: 2 in the Sequence Listing:
  a valine residue substituted for an isoleucine residue at position 30;
  an aspartic acid residue substituted for an asparagine residue at position 33;
  an arginine residue substituted for a glycine residue at position 36; and
  a methionine residue substituted for the leucine residue at position 154.

[18] The mutant xylanase according to [15], wherein the mutant xylanase includes at least the following substitute amino acid residues in the amino acid sequence represented by SEQ ID NO: 2 in the Sequence Listing:
  a valine residue substituted for an isoleucine residue at position 30;
  a threonine residue substituted for a serine residue at position 59;
  a methionine residue substituted for the leucine residue at position 154;
  a histidine residue substituted for a tyrosine residue at position 239; and
  a serine residue substituted for a cysteine residue at position 242.
[19] A nucleic acid represented by a base sequence encoding the amino acid sequence of the mutant xylanase according to any one of [13] to [18].
[20] An expression vector including the nucleic acid according to [19].
[21] A transformant including the expression vector according to [20].
[22] The transformant according to [21], wherein a host cell of the transformant is a cell derived from *Escherichia coli*, *Bacillus subtilis*, yeast, an actinomycete, or a filamentous fungus.
[23] The transformant according to [22], wherein the filamentous fungus belongs to the genus *Trichoderma*, the genus *Acremonium*, the genus *Humicola*, or the genus *Aspergillus*.
[24] The transformant according to [22] or [23], wherein the filamentous fungus is *Trichoderma viride*, *Acremonium cellulolyticus*, *Humicola insolens*, or *Aspergillus niger*.
[25] A method of producing a mutant xylanase, the method including culturing the transformant according to any one of [21] to [24] and recovering the mutant xylanase according to any one of [13] to [18] from at least one of the cultured transformant or a culture product of the transformant.
[26] A mutant xylanase produced by the production method according to [25].
[27] A composition including the mutant xylanase according to any one of [13] to [18] and [21].
[28] A method of bleaching a pulp, the method including contacting the mutant xylanase according to any one of [13] to [18] and [21] with the pulp.
[29] A detergent including the mutant xylanase according to any one of [13] to [18] and [21].
[30] An animal feed including the mutant xylanase according to any one of [13] to [18] and [21].
[31] A bread-making modifier including the mutant xylanase according to any one of [13] to [18] and [21].

Advantageous Effects of Invention

According to the present invention, an inexpensive and efficient saccharification method for lignocellulose using a thermostable xylanase can be provided. In addition, a mutant xylanase that has a substitute amino acid residue, and that exhibits stable activity even under severe conditions in which enzymes easily inactivate, and that provides an initial rate of reaction not significantly reduced as compared to a wild-type xylanase corresponding to the mutant xylanase, can also be provided. Furthermore, according to the invention, a production method capable of producing the mutant xylanase at low cost can be provided, and various uses of the mutant xylanase can also be provided.

DESCRIPTION OF EMBODIMENTS

A thermostable xylanase according to the invention may be any thermostable xylanase of which the xylanase activity after heat treatment for a specified period of time is at the same level as that of the xylanase activity before the heat treatment, or of which a reduction in the xylanase activity thereof after heat treatment as compared to the xylanase activity before the heat treatment is small.

Examples thereof include xylanases obtained from filamentous fungi of the genus *Aspergillus*, the genus *Trichoderma*, the genus *Aureobasidium*, the genus *Schizophyllum commune*, or the like, and bacteria of the genus *Bacillus*, the genus *Clostridium*, and the genus *Streptomyces*.

Among the wild-type xylanases described above, those exhibiting a xylanase activity after heat treatment at 50° C. for 24 hours that is at least 50% of the xylanase activity thereof before heat treatment, are preferable.

In addition, the thermostable xylanase according to the invention may be a mutant xylanase obtained by introducing a mutation into a wild-type xylanase, such as those obtained from filamentous fungi and bacteria, so as to improve thermal stability, as necessary. The mutant xylanase is more preferably a mutant xylanase which has an initial rate of reaction that is at least 70% of that provided by a wild-type xylanase corresponding thereto, and of which the xylanase activity after heat treatment at 50° C. for 24 hours is at least 50% of its xylanase activity thereof before the heat treatment, and which includes a substitute amino acid.

A nucleic acid according to the invention is a nucleic acid represented by a base sequence encoding an amino acid sequence of the mutant xylanase described above.

An expression vector according to the invention includes a nucleic acid represented by a base sequence encoding an amino acid sequence of the mutant xylanase.

A host cell according to the invention is a cell which is transformed with the expression vector including a nucleic acid represented by a base sequence encoding an amino acid sequence of the mutant xylanase.

A method of producing a mutant xylanase according to the invention includes culturing the host cell and collecting the mutant xylanase from at least one of the cultured host cell or a culture product of the host cell. The mutant xylanase according to the invention also includes a mutant xylanase produced by the above-described method of producing a mutant xylanase.

A composition according to the invention includes the mutant xylanase.

A method of producing a saccharified product of lignocellulose according to the invention includes contacting the mutant xylanase with a lignocellulosic raw material.

A method of bleaching pulp according to the invention includes contacting the mutant xylanase with the pulp.

A detergent, an animal feed, or a bread-making modifier according to the invention includes the mutant xylanase.

In the invention, descriptions about an amino acid sequence and a base sequence encoding the mutant xylanase or individual sequences of primers shall apply to the respective mentioned sequences as well as sequences complementary thereto, based on the mutually complementary relationship therebetween, unless otherwise specified. When the descriptions in the invention are applied to the sequences complementary to the respective sequences mentioned, the descriptions shall be interpreted, throughout the specification, as if sequences recognized by the complementary sequences were sequences complementary to corresponding sequences mentioned in the present specification, within a range of common technical knowledge of those skilled in the art.

As used herein, the scope of the term "process" includes not only an independent process but also a process that is not clearly distinguished from other processes as long as the expected purpose of the process is achieved.

In the specification, the numerical range indicated by "(from) . . . to . . . " indicates a range including the numerical values described before and after "to" as the minimum and maximum values, respectively.

In the specification, when two or more substances, each corresponding to a particular component of a composition, are present, the amount of the particular component in the composition means the total amount of the two or more substances present in the composition, unless otherwise specified.

Hereinafter, the invention will be described.

(1) DEFINITIONS

Definitions of Xylanase Activity and Initial Rate of Reaction

In the invention, the term "xylanase activity" means producing of an oligosaccharide having a reducing end (hereinafter also referred to as simply "reducing sugar") through random hydrolysis of β-1,4 bonds of xylan, which mainly constitutes plant cell walls.

In the invention, the term "initial rate of reaction" means an initial rate of reaction of xylanase activity.

The initial rate of reaction can be determined in the following manner. First, into 100 mM a sodium citrate buffer solution (pH 4.5), 1% (w/w) birchwood xylan (manufactured by Sigma-Aldrich Co. LLC), which is a substrate, is vigorously mixed. Then, centrifugation at 5000×g for 15 minutes was performed, to prepare a supernatant from which residual xylan present in the sodium citrate buffer solution has been removed. Next, into the supernatant as a substrate solution, xylanase is mixed in an amount of 0.1% (w/w) with respect to the substrate solution. The mixture is allowed to react while being stirred at 45° C. for 30 minutes, and the amount of reducing saccharide in the obtained reaction solution is measured by the DNS method (Bailey et al., 1992), whereby the initial rate of reaction of the xylanase activity can be obtained.

Definition of Activity Equivalent to that of Wild-Type

As used herein, the expression "activity equivalent to that of wild-type" means that the initial rate of reaction of a mutant xylanase is 0.7 (70%) or higher provided that the initial rate of reaction of a wild-type xylanase thereof is assumed to be 1.

Definition of Range in which Enzyme Stably Works

As used herein, the expression "range in which enzyme stably works" means a range having a temperature higher than 30° C. but lower than 40° C. and a pH larger than 6 but smaller than 8.

As used herein, the expression "severe conditions in which enzymes easily inactivate" means an acidic region (from pH 4 to pH 6), a basic region (from pH 8 to pH 10), and a high-temperature region (from 40° C. to 80° C.).

Definitions of Residual Activity and Stability

As used herein, the term "residual activity" refers to quotient, expressed in percentage, obtained by dividing an initial rate of reaction after an enzyme is exposed for a certain period of time to a condition outside the range in which the enzyme stably works, by an initial rate of reaction before the exposure. A specific measurement method is as follows: after heating treatment is performed at 50° C. and pH 4.5 for varied periods of 16 hours, 24 hours, 48 hours, and 72 hours, standing still on ice is performed for 5 minutes, and the initial rate of reaction is measured. The initial rate achieved by the enzyme before the heat treatment is also measured. Then, the division calculation is performed and the resultant value is expressed in percentage. In addition to the above, residual activities are measured in the same manner with respect to initial rates of reaction after heating treatment is performed at 50° C. for 1 hour at pH 8, pH 9, and pH 10, respectively, initial rates of reaction after heating treatment is performed at 60° C. for 1 hour at pH 8, pH 9, and pH 10, respectively, and an initial rate of reaction after heating treatment is performed at 70° C. and pH 5.5 for 5 minutes.

In the present specification, stability is determined by the degree of residual activity observed when the enzyme has been exposed to severe conditions in which enzymes easily inactivate.

(2) MUTANT XYLANASE ACCORDING TO THE INVENTION

The mutant xylanase according to the invention provides an initial rate of reaction that is at least 70% of that provided by a wild-type xylanase corresponding thereto, has a xylanase activity after heat treatment at 50° C. for 24 hours that is at least 50% of its xylanase activity before the heat treatment, and has a substitute amino acid residue.

Since the mutant xylanase according to the invention has a substitute amino acid residue, the mutant xylanase exhibits stable activity even under severe conditions in which enzymes easily inactivate, and the initial rate of reaction thereof is not significantly reduced as compared to a wild-type xylanase corresponding thereto.

The mutant xylanase according to the invention may be any mutant xylanase which provides an initial rate of reaction that is at least 70% of that provided by a wild-type xylanase corresponding thereto, and which has a xylanase activity after heat treatment at 50° C. for 24 hours that is at least 50% of its xylanase activity before the heat treatment, and which has a substitute amino acid residue, and is not particularly limited in other respects.

The mutant xylanase according to the invention preferably provides an initial rate of reaction that is at least 70% of that provided by a wild-type xylanase corresponding thereto.

When the initial rate of reaction is 70% or higher, the amount of the mutant xylanase to be used does not become large as compared to the usage amount of a wild-type xylanase corresponding to the mutant xylanase, and therefore an initial rate of reaction of 70% or higher is preferable in industrial applications.

The xylanase activity of the mutant xylanase according to the invention after heat treatment at 50° C. for 24 hours is preferably at least 50%, and more preferably at least 70%, of its xylanase activity before the heat treatment.

A xylanase activity after heat treatment at 50° C. for 24 hours of at least 50% of its xylanase activity before the heat treatment is preferable because the mutant xylanase can be used in a range in which the enzyme stably works. Specifically, in cases in which an enzyme reaction over a long time such as saccharification of lignocellulose or reutilization of an enzyme is needed, a xylanase activity after the heat treatment that satisfies the above condition removes necessity to add a large amount of the enzyme in order to maintain an initial rate of reaction thereof observed at the initiation of the reaction, thereby avoiding an increase in the cost; thus, a xylanase activity after the heat treatment that satisfies the above condition is preferable also from the economical viewpoint.

The origin of the mutant xylanase according to the invention is not particularly limited. Examples of the mutant xylanase include those derived from a *Bacillus subtilis*, a bacterium of the genus *Clostridium*, an actinomycete, a filamentous fungus, and a basidiomycete. From the viewpoint of industrial applications, mutant xylanases derived from the genus *Trichoderma*, the genus *Acremonium*, the genus *Humicola*, or the genus *Aspergillus*, among filamentous fungi, are preferable. From the viewpoint of mass production, mutant xylanases derived from *Trichoderma viride*, *Acremonium cellulolyticus*, *Humicola insolens*, or *Aspergillus niger* are more preferable.

More preferable mutant xylanases include the two mutant xylanases described below, from the viewpoints that stable activity is exhibited even under severe conditions in which enzymes easily inactivate, and that an initial rate of reaction not significantly reduced as compared to a wild-type xylanase corresponding thereto is provided.

A first preferable mutant xylanase is a mutant xylanase derived from xylanase of a filamentous fungus of the genus *Trichoderma*.

The first preferable mutant xylanase is preferably a mutant xylanase derived from xylanase of *Trichoderma viride* from the viewpoints that the initial rate of reaction is at least 70% of that provided by a wild-type xylanase corresponding thereto, and that the xylanase activity after heat treatment at 50° C. for 24 hours is at least 50% of its xylanase activity before the heat treatment.

The first preferable mutant xylanase may be a mutant xylanase having, in the amino acid sequence of SEQ ID NO: 1 in the Sequence Listing, the following substitute amino acid residues: a leucine residue substituted for an asparagine residue at position 29; an arginine residue substituted for a lysine residue at position 58; an amino acid residue, other than a tyrosine residue, substituted for a tyrosine residue at position 27; and an amino acid residue, other than an asparagine residue, substituted for an asparagine residue at position 44. from the viewpoints of providing an initial rate of reaction that is at least 70% of that provided by a wild-type xylanase corresponding thereto, and facilitating achievement of a xylanase activity after heat treatment at 50° C. for 24 hours that is at least 50% of its xylanase activity before the heat treatment.

The amino acid sequence of SEQ ID NO: 1 in the Sequence Listing is an amino acid sequence encoding xylanase II of *Trichoderma viride*.

A second preferable mutant xylanase may be a mutant xylanase derived from xylanase of a filamentous fungus belonging to the genus *Acremonium*.

The second preferable mutant xylanase is preferably a mutant xylanase derived from xylanase of *Acremonium cellulolyticus* from the viewpoints that the initial rate of reaction is at least 70% of that provided by a wild-type xylanase corresponding thereto and that the xylanase activity after heat treatment at 50° C. for 24 hours is at least 50% of its xylanase activity before the heat treatment.

The amino acid sequence of SEQ ID NO: 2 in the Sequence Listing is an amino acid sequence encoding xylanase I of *Acremonium cellulolyticus*.

The second preferable mutant xylanase preferably includes at least a substitute amino acid residue at position 154 that is a methionine residue substituted for a leucine residue, from the viewpoint of facilitating achievement of an initial rate of reaction of at least 70% of that provided by a wild-type xylanase corresponding thereto, and achievement of a xylanase activity after heat treatment at 50° C. for 24 hours that is at least 50% of its xylanase activity before the heat treatment.

Specific examples of the mutant xylanase according to the invention include those having a substitute amino acid residue and represented by clone Nos. 1 to 17 shown in Table 1. However, the mutant xylanase according to the invention is not limited thereto.

TABLE 1

| Clone No. | Sequence No. (Wild-Type) | Position of Substitute Amino Acid Residue | Before Mutation | After Mutation |
|---|---|---|---|---|
| 1 | 1 | 27 | Tyr | Phe |
|   | 1 | 29 | Asn | Leu |
|   | 1 | 44 | Asn | Ser |
|   | 1 | 58 | Lys | Arg |
| 2 | 2 | 30 | Ile | Val |
| 3 | 2 | 33 | Asn | Asp |
| 4 | 2 | 36 | Gly | Arg |
| 5 | 2 | 59 | Ser | Thr |
| 6 | 2 | 90 | Thr | Ser |
| 7 | 2 | 132 | Gln | Arg |
| 8 | 2 | 154 | Leu | Met |
| 9 | 2 | 174 | Ser | Thr |
| 10 | 2 | 195 | Pro | His |
| 11 | 2 | 197 | Ser | Asn |
| 12 | 2 | 217 | Gly | Glu |
| 13 | 2 | 239 | Tyr | His |
| 14 | 2 | 242 | Cys | Ser |
| 15 | 2 | 33 | Asn | Asp |
|   | 2 | 36 | Gly | Arg |
|   | 2 | 90 | Thr | Ser |
|   | 2 | 132 | Gln | Arg |
|   | 2 | 154 | Leu | Met |
|   | 2 | 174 | Ser | Thr |
|   | 2 | 195 | Pro | His |
|   | 2 | 197 | Ser | Asn |
|   | 2 | 217 | Gly | Glu |
| 16 | 2 | 30 | Ile | Val |
|   | 2 | 33 | Asn | Asp |
|   | 2 | 36 | Gly | Arg |
|   | 2 | 154 | Leu | Met |
| 17 | 2 | 30 | Ile | Val |
|   | 2 | 59 | Ser | Thr |
|   | 2 | 154 | Leu | Met |
|   | 2 | 239 | Tyr | His |
|   | 2 | 242 | Cys | Ser |

In Table 1, from the viewpoint of providing an initial rate of reaction that is at least 70% of that provided by a wild-type xylanase corresponding thereto and a xylanase activity after heat treatment at 50° C. for 24 hours that is at least 50% of its xylanase activity before the heat treatment, a mutant xylanase TVX01 (Clone No. 1), a mutant xylanase ACX 01 (Clone No. 15), a mutant xylanase ACX02 (Clone No. 16), or a mutant xylanase ACX03 (Clone No. 17) is preferable.

The mutant xylanase TVX01 includes the following substitute amino acid residues incorporated into the amino acid sequence of SEQ ID NO: 1 in the Sequence Listing: a leucine residue substituted for an asparagine residue at position 29, an arginine residue substituted for a lysine residue at position 58, a phenylalanine residue substituted for a tyrosine residue at position 27, and a serine residue substituted for an asparagine residue at position 44. The mutant xylanase TVX01 is preferable from the viewpoints of providing an initial rate of reaction that is at least 70% of that provided by a wild-type xylanase corresponding thereto and a xylanase activity after heat treatment at 50° C. for 24 hours that is at least 50% of its xylanase activity before the heat treatment.

The mutant xylanase TVX 01 according to the invention has activity in a range of preferably from 30° C. to 90° C., and more preferably from 30° C. to 70° C. In addition, the mutant xylanase TVX01 has activity in a range of preferably from pH 3 to 9, and more preferably from pH 4 to 7.

The mutant xylanase ACX01 includes a substitute amino acid residue that is an aspartic acid residue substituted for an asparagine residue at position 33, a substitute amino acid residue that is an arginine residue substituted for a glycine residue at position 36, a substitute amino acid residue that is a serine residue substituted for a threonine residue at position 90, a substitute amino acid residue that is an arginine residue substituted for a glutamine residue at position 132, a substitute amino acid residue that is a methionine residue substituted for a leucine residue at position 154, a substitute amino acid residue that is a threonine residue substituted for a serine residue at position 174, a substitute amino acid residue that is a histidine residue substituted for a proline residue at position 195, a substitute amino acid residue that is an asparagine residue substituted for a serine residue at position 197, and a substitute amino acid residue that is a glutamic acid residue substituted for a glycine residue at position 217. The mutant xylanase ACX01 is preferable from the viewpoints of an initial rate of reaction that is at least 70% of that provided by a wild-type xylanase corresponding thereto and a xylanase activity after heat treatment at 50° C. for 24 hours that is at least 50% of its xylanase activity before the heat treatment.

The mutant xylanase ACX01 according to the invention has activity in a range of preferably from 30° C. to 80° C., and more preferably 30° C. to 65° C. In addition, the mutant xylanase ACX01 has activity in a range of preferably from pH 2 to 8, and more preferably from pH 2 to 5.

The mutant xylanase ACX02 includes a substitute amino acid residue that is a valine residue substituted for an isoleucine residue at position 30, a substitute amino acid residue that is an aspartic acid residue substituted for an asparagine residue at position 33, a substitute amino acid residue that is an arginine residue substituted for a glycine residue at position 36, and a substitute amino acid residue that is a methionine residue substituted for a leucine residue at position 154. The mutant xylanase ACX02 is preferable from the viewpoints of providing an initial rate of reaction that is at least 70% of that provided by a wild-type xylanase corresponding thereto and a xylanase activity after heat treatment at 50° C. for 24 hours that is at least 50% of its xylanase activity before the heat treatment.

The mutant xylanase ACX02 according to the invention has activity in a range of preferably from 30° C. to 80° C., and more preferably from 30° C. to 65° C. In addition, the mutant xylanase ACX02 has activity in a range of preferably from pH 2 to 8, and more preferably from pH 2 to 5.

The mutant xylanase ACX03 includes a substitute amino acid residue that is a valine residue substituted for an isoleucine residue at position 30, a substitute amino acid residue that is a threonine residue substituted for a serine residue at position 59, a substitute amino acid residue that is a methionine residue substituted for a leucine residue at position 154, a substitute amino acid residue that is a histidine residue substituted for a tyrosine residue at position 239, and a substitute amino acid residue that is a serine residue substituted for a cysteine residue at position 242.

The mutant xylanase ACX03 is preferable from the viewpoints of providing an initial rate of reaction that is at least 70% of that provided by a wild-type xylanase corresponding thereto and a xylanase activity after heat treatment at 50° C. for 24 hours that is at least 50% of its xylanase activity before the heat treatment.

The mutant xylanase ACX03 according to the invention has activity in a range of preferably from 30° C. to 80° C., and more preferably from 30° C. to 65° C. In addition, the mutant xylanase ACX03 has activity in a range of preferably from pH 2 to 8, and more preferably from pH 2 to 5.

The scope of the mutant xylanase according to the invention also includes mutant xylanases consisting of amino acid sequences homologous to the mutant xylanase TVX01.

The "amino acid sequences homologous thereto" may be, for example, amino acid sequences that exhibit approximately equivalent level of xylanase activity as that of the mutant xylanase TVX01. Preferable examples include mutant xylanases having a homology of 80% or higher, more preferably 90% or higher, and still more preferably 95% or higher, with the amino acid sequence of the mutant xylanase TVX01. A homology of 80% or higher is considered to provide a higher similarity between the steric structures of the xylanases, thereby providing an advantage in that, for example, a mutant xylanase exhibiting approximately equivalent level of activity as that according to the invention can be developed by introducing one or more mutation sites clarified by the invention.

The same applies to the mutant xylanases ACX01, ACX02, and ACX03, in addition to the mutant xylanase TVX01.

The scope of the mutant xylanase TVX01 according to the invention also encompasses mutant xylanases in which insertion, deletion, or substitution of one or more amino acid residues has been introduced into the amino acid sequence encoding the mutant xylanase TVX01, and which exhibit approximately equivalent level of activity as that of the mutant xylanase TVX01.

In cases in which one or more amino acid residues are inserted, deleted, or substituted, the position(s) of the insertion, the deletion, or the substitution may be freely selected as long as the effects exerted by the invention are not impaired. The number of amino acid residues that are inserted, deleted, or substituted may be one amino acid residue, or two or more amino acid residues, for example, from one amino acid residue to ten amino acid residues, preferably from one amino acid residue to five amino acid residues. Specific examples include: a mutant xylanase in which the mutations at the four sites as well as substitution of a glycine residue at position 47 with a cysteine residue have been introduced into the amino acid sequence of SEQ ID NO: 1 in the Sequence Listing; a mutant xylanase in which the mutations at the four sites as well as substitution of a glutamine residue at position 52 with a lysine residue have been introduced into the amino acid sequence of SEQ ID NO: 1 in the Sequence Listing; a mutant xylanase in which the mutations at the four sites as well as substitution of an valine residue at position 59 with an isoleucine residue have been introduced into the amino acid sequence of SEQ ID NO: 1 in the Sequence Listing; a mutant xylanase in which the mutations at the four sites as well as substitution of an asparagine residue at position 67 with an aspartic acid residue have been introduced into the amino acid sequence of SEQ ID NO:1 in the Sequence Listing; a mutant xylanase in which the mutations at the four sites as well as substitution of an asparagine residue at position 69 with an isoleucine residue have been introduced into the amino acid sequence of SEQ ID NO: 1 in the Sequence Listing; a mutant xylanase in which the mutations at the four sites as well as substitution of an serine residue at position 80 with an alanine residue have been introduced into the amino acid sequence of SEQ ID NO: 1 in the Sequence Listing; a mutant xylanase in which the mutations at the four sites as well as substitution of an asparagine residue at position 97 with an aspartic acid residue have been introduced into the amino acid sequence of SEQ ID NO: 1 in the Sequence Listing; a mutant xylanase in which the mutations at the four sites as well as substitution of a leucine residue at position 105 with a methionine residue have been introduced into the amino acid sequence of SEQ ID NO: 1 in the Sequence Listing; a mutant xylanase in which the mutations at the four sites as well as substitution of an threonine residue at position 109 with an alanine residue have been introduced into the amino acid sequence of SEQ ID NO: 1 in the Sequence Listing; a mutant xylanase in which the mutations at the four sites as well as substitution of an threonine residue at position 120 with an arginine residue have been introduced into the amino acid sequence of SEQ ID NO: 1 in the Sequence Listing; a mutant xylanase in which the mutations at the four sites as well as substitution of an threonine residue at position 143 with an isoleucine residue have been introduced into the amino acid sequence of SEQ ID NO: 1 in the Sequence Listing; a mutant xylanase in which the mutations at the four sites as well as substitution of an asparagine residue at position 151 with a serine residue have been introduced into the amino acid sequence of SEQ ID NO: 1 in the Sequence Listing; a mutant xylanase in which the mutations at the four sites as well as substitution of a serine residue at position 161 with a leucine residue have been introduced into the amino acid sequence of SEQ ID NO: 1 in the Sequence Listing; and a mutant xylanase in which the mutations at the four sites as well as substitution of a serine residue at position 186 with a threonine residue have been introduced into the amino acid sequence of SEQ ID NO: 1 in the Sequence Listing.

The same applies to the mutant xylanases ACX01, ACX02, and ACX03, in addition to the mutant xylanase TVX01. Specific examples include a mutant xylanase in which the mutation sites defined in the ACX01 as well as substitution of a serine residue at position 133 with an asparagine residue have been introduced into the amino acid sequence of SEQ ID NO: 2 in the Sequence Listing, and a mutant xylanase in which the mutation sites defined in the ACX01 as well as substitution of a glutamine residue at position 176 with an arginine residue have been introduced into the amino acid sequence of SEQ ID NO: 2 in the Sequence Listing.

Similarly, regarding the mutant xylanase ACX02, many mutants having all of the mutation sites defined in the ACX02 exhibit properties approximately equivalent to those of the ACX02. Specific examples thereof include: a mutant xylanase in which the mutation sites defined in ACX02 as well as substitution of a threonine residue at position 90 with a serine residue have been introduced into the amino acid sequence of SEQ ID: NO: 2 in the Sequence Listing; a mutant xylanase in which the mutation sites defined in ACX02 as well as substitution of a glutamine residue at position 132 with an arginine residue have been introduced into the amino acid sequence of SEQ ID: NO: 2 in the Sequence Listing; a mutant xylanase in which the mutation sites defined in ACX02 as well as substitution of a serine residue at position 133 with an asparagine residue have been introduced into the amino acid sequence of SEQ ID: NO: 2 in the Sequence Listing; a mutant xylanase in which the mutation sites defined in ACX02 as well as substitution of a serine residue at position 174 with a threonine residue have been introduced into the amino acid sequence of SEQ ID: NO: 2 in the Sequence Listing; a mutant xylanase in which the mutation sites defined in ACX02 as well as substitution of a proline residue at position 195 with a histidine residue have been introduced into the amino acid sequence of SEQ ID: NO: 2 in the Sequence Listing; a mutant xylanase in which the mutation sites defined in ACX02 as well as substitution of a glutamine residue at position 176 with an arginine residue have been introduced into the amino acid sequence of SEQ ID: NO: 2 in the Sequence Listing; a mutant xylanase in which the mutation sites defined in ACX02 as well as substitution of a serine residue at position 197 with an asparagine residue have been introduced into the amino acid sequence of SEQ ID: NO: 2 in the Sequence Listing; and a mutant xylanase in which the mutation sites defined in ACX02 as well as substitution of a glycine residue at position 217 with a glutamic acid residue have been introduced into the amino acid sequence of SEQ ID: NO: 2 in the Sequence Listing.

Furthermore, many mutants having all of the mutation sites defined in the mutant xylanase ACX03 exhibit properties approximately equivalent to those of the ACX03. Specific examples thereof include a mutant xylanase in which the mutation sites defined in ACX03 as well as substitution of a glutamine residue at position 176 with an arginine residue have been introduced into the amino acid sequence of SEQ ID: NO: 2 in the Sequence Listing.

The mutant xylanase according to the invention can be synthesized according to known methods. Examples of a method for generating a mutation in a gene include site-directed mutagenesis (Kramer, W. and frita, H. J., Methods in Enzymology, vol. 154, P. 350 (1987)), recombinant PCR (PCR Technology, Stockton Press (1989)), chemical synthesis of DNA of a specific site, hydroxylamine treatment of the gene, and a method including treating a microorganism having the gene with UV irradiation or a chemical agent such as nitrosoguanidine or nitrous acid. Among methods for obtaining the mutant xylanase according to the invention, preferable methods include the method of producing a mutant xylanase described below.

(3) METHOD OF PRODUCING MUTANT XYLANASE

A method of producing a mutant xylanase according to the invention (hereinafter referred to as simply "production method") includes culturing a transformant and recovering the mutant xylanase from at least one of the cultured transformant or a culture product of the transformant.

Here, the term "transformant" refers to a transformant transformed with an expression vector that includes a nucleic acid represented by a base sequence encoding the amino acid sequence of the mutant xylanase.

In a method of producing a mutant xylanase according to the invention includes culturing a transformant transformed with an expression vector that includes a nucleic acid represented by a base sequence encoding the amino acid sequence of the mutant xylanase, to produce the mutant xylanase. With this production method, a mutant xylanase that exhibits stable activity even under severe conditions in which enzymes easily inactivate, and that provides an initial rate of reaction not significantly reduced as compared to a wild-type xylanase corresponding thereto, can be produced at low cost.

Processes that may be included in the production method are described below. The method of producing a mutant xylanase according to the invention includes a process of culturing a transformant transformed with an expression vector that includes a nucleic acid represented by a base sequence encoding the amino acid sequence of the mutant xylanase (a host cell cultivation process) and a process of recovering the mutant xylanase from at least one of the cultured transformant or a culture product of the transformant (a mutant xylanase recovery process). The method of producing a mutant xylanase according to the invention may further include other processes, as necessary.

A. Transformant Cultivation Process

The transformant cultivation process is a process of culturing a transformant transformed with an expression vector that includes a nucleic acid represented by a base sequence encoding the amino acid sequence of the mutant xylanase.

[Transformant]

In the production method according to the invention, the transformant is transformed with an expression vector that includes a nucleic acid represented by a base sequence encoding the amino acid sequence of the mutant xylanase, and the transformant is not particularly limited in other respects.

Examples of the transformant include host cells derived from *Escherichia coli*, *Bacillus subtilis*, yeasts, actinomycetes, filamentous fungi, or the like. Among them, transformants of which the host cells are derived from *Bacillus subtilis*, yeasts, actinomycetes, or filamentous fungi, each enabling production of the target enzyme by secretion to outside their cells, are preferable from the viewpoint of industrial applications.

Examples of the yeasts include those belonging to the genus *Saccharomyces*, the genus *Hansenula*, or the genus *Pichia*. One example of preferable yeasts is *Saccharomyces cerevisiae*.

Examples of the filamentous fungi include those belonging to the genus *Humicola*, the genus *Aspergillus*, the genus *Trichoderma*, or the genus *Acremonium*. Preferable examples of the filamentous fungi are *Humicola insolens*, *Aspergillus niger*, *Aspergillus oryzae*, *Trichoderma viride*, or *Acremonium cellulolyticus*. From the viewpoint of industrial applications, *Trichoderma viride*, *Acremonium cellulolyticus*, *Humicola insolens*, or *Aspergillus niger* is more preferable.

[Nucleic Acid]

The nucleic acid described above is represented by a base sequence encoding the amino acid sequence of the mutant xylanase.

Examples of methods for synthesizing the base sequence encoding the amino acid sequence of the mutant xylanase include a method of introducing one or more mutation sites into a base sequence encoding a corresponding wild-type xylanase, and a method of chemically synthesizing the entire base sequence that includes one or more mutation sites. The method of introducing one or more mutation sites into a base sequence encoding a corresponding wild-type xylanase is described below using a base sequence encoding a xylanase I of *Acremonium cellulolyticus* and a base sequence encoding a xylanase II of *Trichoderma viride*. However, the nucleic acid according to the invention is not limited thereto.

[Introduction of Mutation Sites into Base Sequence Encoding Wild-Type Xylanase]

Examples of the base sequences encoding the wild-type xylanases include a base sequence encoding the xylanase I of *Acremonium cellulolyticus* represented by SEQ ID NO: 3 in the Sequence Listing and a base sequence encoding the xylanase II of *Trichoderma viride* represented by SEQ ID NO: 4 in the Sequence Listing.

Examples of a method of generating a mutation in a gene using a base sequence encoding a wild-type xylanase such as those mentioned above as a template include a site-directed mutagenesis method (Kramer, W. and frita H. J., Methods in Enzymology, vol. 154, P. 350 (1987)), a recombinant PCR method (PCR Technology, Stockton Press (1989)), a method of chemically synthesizing a particular portion of a DNA, a method of treating a gene with hydroxylamine, a method of subjecting a microorganism possessing the gene to UV irradiation treatment or to treatment with a chemical agent such as nitrosoguanidine or nitrous acid, and commercially available kits for introducing mutations. A mutation can be introduced into the base sequence using these methods.

The positions and types of introduced mutations are not particularly limited. The mutation sites of the clones represented by Clone Nos. 1 to 17 are indicated as specific examples in Table 2 below. However, the positions and types of introduced mutations are not limited thereto.

TABLE 2

| Clone No. | SEQ ID NO: (Wild-type) | Positions of Bases | Before Mutation | After Mutation |
|---|---|---|---|---|
| 1 | 1 | 79 to 81 | TAC | TTC, TTT |
|   | 1 | 85 to 87 | AAT | CTC, TTA, TTG, CTT, CTA, CTG |
|   | 1 | 130 to 132 | AAC | AGC, TCT, TCC, TCA, TCG, AGT |
|   | 1 | 172 to 174 | AAG | AGG, CTG, CGC, CGA, CGG, AGA |
| 2 | 2 | 88 to 90 | ATC | GTC, GTT, GTA, GTG |
| 3 | 2 | 97 to 99 | AAT | GAT, GAC |
| 4 | 2 | 106 to 108 | GGG | AGG, CTG, CGA, CGC, CGG, AGA |
| 5 | 2 | 175 to 177 | TCG | ACG, ACT, ACC, ACA |
| 6 | 2 | 268 to 270 | ACT | TCT, TCC, TCA, TCG, AGT, AGC |
| 7 | 2 | 394 to 396 | CAA | CGA, CTG, CGC, CGG, AGA, AGG |
| 8 | 2 | 460 to 462 | TTG | ATG |
| 9 | 2 | 520 to 522 | TCT | ACT, ACC, ACA, ACG |

TABLE 2-continued

| Clone No. | SEQ ID NO: (Wild-type) | Positions of Bases | Before Mutation | After Mutation |
|---|---|---|---|---|
| 10 | 2 | 583 to 585 | CCC | CAC, CAT |
| 11 | 2 | 589 to 591 | AGC | AAC, AAT |
| 12 | 2 | 649 to 651 | GGA | GAA, GAG |
| 13 | 2 | 715 to 717 | TAC | CAC, CAT |
| 14 | 2 | 724 to 726 | AGC | AGC, TCT, TCC, TCA, TCG, AGT |
| 15 | 2 | 97 to 99 | AAT | GAT, GAC |
|  | 2 | 106 to 108 | GGG | AGG, CTG, CGC, CGA, CGG, AGA |
|  | 2 | 268 to 270 | ACT | TCT, TCC, TCA, TCG, AGT, AGC |
|  | 2 | 394 to 396 | CAA | CGA, CTG, CGC, CGG, AGA, AGG |
|  | 2 | 460 to 462 | TTG | ATG |
|  | 2 | 520 to 522 | TCT | ACT, ACC, ACA, ACG |
|  | 2 | 583 to 585 | CCC | CAC, CAT |
|  | 2 | 589 to 591 | AGC | AAC, AAT |
|  | 2 | 649 to 651 | GGA | GAA, GAG |
| 16 | 2 | 88 to 90 | ATC | GTC, GTT, GTA, GTG |
|  | 2 | 97 to 99 | AAT | GAT, GAC |
|  | 2 | 106 to 108 | GGG | AGG, CTG, CGA, CGC, CGG, AGA |
|  | 2 | 460 to 462 | TTG | ATG |
| 17 | 2 | 88 to 90 | ATC | GTC, GTT, GTA, GTG |
|  | 2 | 175 to 177 | TCG | ACG, ACT, ACC, ACA |
|  | 2 | 460 to 462 | TTG | ATG |
|  | 2 | 715 to 717 | TAC | CAC, CAT |
|  | 2 | 724 to 726 | AGC | AGC, TCT, TCC, TCA, TCG, AGT |

[Expression Vector]

The expression vector includes a nucleic acid represented by a base sequence encoding the amino acid sequence of the mutant xylanase, and is not particularly limited in other respects. From the viewpoint of improving transformation efficiency or translation efficiency, the expression vector is more preferably a plasmid vector or a phage vector, each of which has a structure as discussed below.

[Basic Structure of Expression Vector]

The expression vector includes a base sequence encoding the mutant xylanase and is capable of transforming the host cell, and the expression vector is not particularly limited in other respects. In addition to the base sequence described above, the expression vector may further include a base sequence that constitutes another region (hereinafter referred to as simply "another region"), if necessary.

Examples of the another region include a control region necessary for the transformant to produce the mutant xylanase and a region necessary for autonomous replication.

From the viewpoint of facilitating the selection of the transformant, the expression vector may further include a base sequence encoding a gene for selection that can serve as a selection marker.

Examples of the control region necessary to produce the mutant xylanase include a promoter sequence (including an operator sequence that controls transcription), a ribosome binding sequence (SD sequence), and a transcription terminator sequence.

[Expression Vector in Case where Host Cell is Yeast]

In cases in which yeast is used as a host cell, the expression vector preferably includes a promoter sequence in addition to the base sequence encoding the mutant xylanase, from the viewpoint of efficiency of production of the mutant xylanase. The promoter sequence may be any sequence that allows the expression of the mutant xylanase in a transformant of which the host cell is yeast.

For example, promoter sequences, such as an alcohol dehydrogenase (ADH1) promoter, a phosphoglycerate kinase (PGK1) promoter, a peptide chain elongation factor (TEF) promoter, a glycerol-3-phosphate dehydrogenase (GPD) promoter, a galactokinase (GAL1) promoter, a metallothionein (CUP1) promoter, a repressible acid phosphatase (PHO5) promoter, and a glyceraldehyde-3-phosphate dehydrogenase (GAPDH) promoter, are employed.

The origins of the promoter sequences are not limited to the yeast, which serves as the host cell.

Exogenous promoters such as a cytomegalovirus (CMV) promoter may be used. These promoters may be selected, as appropriate, in accordance with the origin and type of the enzyme to be used.

The expression vector may also include a secretion signal. Inclusion of the secretion signal allows the mutation xylanase to be secreted to outside the cell when the transformant has produced the mutant xylanase.

The secretion signal should allow the mutant xylanase to be secreted from the yeast serving as the host cell, and is not particularly limited in other respects. From the viewpoint of secretion efficiency, it is preferable to use an a factor signal sequence, an invertase signal sequence, an acid phosphatase signal sequence, a glucoamylase signal sequence, or the like.

Specific examples of expression vectors that include a promoter sequence or a secretion signal, such as those described above, include pRS423, pRS424, and YEplac195.

[Expression Vector in Case where Host Cell is Filamentous Fungus]

In cases in which a filamentous fungus is used as a host cell, the expression vector preferably includes a promoter sequence in addition to the base sequence encoding the mutant xylanase, from the viewpoint of the efficiency of production of the mutant xylanase. The promoter sequence may be any sequence that allows the expression of the mutant xylanase in a transformant of which the host cell is a filamentous fungus.

Expression vectors suitable for filamentous fungi are described in van den Hondel, C. A. M. J. J. et al. (1991) In: Bennett, J. W. and Lasure, L. L. (eds.) More gene Manipulations in Fungi. Academic Press, pp. 396-428.

In addition, other commonly used expression vectors are also usable, such as pUC18, pBR322, pUC100, pSL1180 (manufactured by Pharmacia, Inc.), pFB6, *Aspergillus* pRAX, and *Trichoderma* pTEX.

[Expression Vector in Case where Host Cell is Prokaryote]

In cases in which the host cell is a prokaryote such as *Escherichia coli*, *Bacillus subtilis*, or an actinomycete, the expression vector preferably includes a promoter sequence in addition to the base sequence encoding the mutant xylanase, from the viewpoint of the efficiency of production of the mutant xylanase. Besides the promoter sequence, the expression vector may include a ribosome binding sequence, a transcription terminator sequence, or the like.

Examples of the promoter sequence include a tryptophan operon (trp) promoter and a lactose operon (lac) promoter, which are derived from *Escherichia coli*, a PL promoter and a PR promoter, which are derived from lambda phage, a gluconic acid synthetase promoter (gnt), an alkaline protease promoter (apr), a neutral protease promoter (npr), and an α-amylase promoter (amy), which are derived from *Bacillus subtilis*.

Independently modified or designed promoter sequences, such as a tac promoter, is also usable.

The ribosome binding sequence may be a sequence derived from *Escherichia coli* or *Bacillus subtilis*. The ribosome binding sequence should function in a desired host cell, such as in *Escherichia coli* or *Bacillus subtilis*, but is not particularly limited in other respects.

Examples of the ribosome binding sequence include a consensus sequence that consists of four or more consecutive bases in a sequence complementary to the 3' end region of 16S ribosome RNA and that has been produced by DNA synthesis.

The transcription terminator sequence is not essential. Transcription terminator sequences that are not dependent on p factor, such as a lipoprotein terminator and a trp operon terminator, may be used.

The order in which these control regions are arranged in the expression vector is not particularly limited. In consideration of transcription efficiency, it is preferable that a promoter sequence, a ribosome binding sequence, a gene encoding a target protein, and a transcription terminator sequence are arranged in this order from the upstream at the 5'-terminal side.

In regard to specific examples of expression vectors as used herein, pBR322, pUC18, Bluescript II SK(+), pKK223-3, and pSC101, which have a region capable of autonomously replicating in *Escherichia coli*, and pUB110, pTZ4, pC194, ρ11, φ1, and φ105, which have a region capable of autonomously replicating in *Bacillus subtilis*, may be utilized as the expression vectors.

In addition, in regard to examples of expression vectors capable of autonomous replication in two or more types of host cells, pHV14, TRp7, YEp7, pBS7, and the like may be used as the expression vectors.

[Method of Producing Transformant]

The transformant according to the invention can be produced by known methods. Examples thereof include a method including constructing an expression vector that includes a base sequence encoding the mutant xylanase according to the invention and that optionally includes the another region, and transforming a desired host cell with the expression vector. Specifically, general methods known in the fields of molecular biology, bioengineering, and genetic engineering may be employed, such as those described in Sambrook, J., et. al., "Molecular Cloning A Laboratory Manual, 3rd Edition", Cold Spring Harbor Laboratory Press, (2001).

The transformant according to the invention may be produced by, for example, incorporating a silent mutation such that a codon having low frequency of use in the host cell is replaced by a codon having high frequency of use in the host cell, in accordance with the necessity, in addition to incorporating the expression vector into the host cell.

There is a possibility that the production amount of the protein derived from the mutant xylanase incorporated in the expression vector is increased thereby.

Table 3 below illustrates an example of the manners in which silent mutations are introduced. Methods for introduction of silent mutations are not particularly limited with respect to technique, mutation sites, types of bases to be changed, and the like as long as the methods enable modification of the codons of the xylanase gene in the expression vector and the codons of the signal sequence for causing secretion of the xylanase gene to the outside of the cell, based on the usage frequencies of the codons in the host cell.

Table 3 below indicates the base positions at which silent mutations are added in order to allow expression of the mutation xylanase ACX02 at high frequency in *T. viride*, and the types of the bases to be changed.

In Table 3, the "base positions" for the sequence name "ACX02" indicate the positions of bases in SEQ ID NO: 4. The "base positions" for the sequence name "*A. cellulolyticus* signal sequence" indicates the positions of bases in SEQ ID NO: 73.

TABLE 3

| Sequence Name | Base Positions | Before Change | After Change |
|---|---|---|---|
| *A. cellulolyticus* signal sequence | 12 | A | C |
| | 42 | G | T |
| | 66 | A | C |
| | 90 | G | C |
| ACX02 | 37 | A | T |
| | 38 | G | C |
| | 39 | T | C |
| | 78 | T | A |
| | 81 | T | C |
| | 106 | A | C |
| | 108 | G | C |
| | 138 | A | C |
| | 279 | A | C |
| | 312 | A | C |
| | 405 | G | C |
| | 474 | A | C |
| | 495 | A | C |
| | 552 | T | C |
| | 573 | A | C |
| | 648 | G | A |
| | 663 | C | G |
| | 718 | A | T |
| | 719 | G | C |
| | 720 | T | C |

[Method of Culturing Transformant]

Conditions for culturing a transformant obtained by transformation with the expression vector are as described in the explanation of the conditions for culturing a host cell before transformation, and known conditions may be used.

In regard to the culture medium, both of a synthesized medium or a natural medium are usable, provided that the medium contains a carbon source, a nitrogen source, an inorganic substance, and other nutrients in appropriate amounts. Known components for culture media may be employed. For example, organic nutritional sources such as meat extract, yeast extract, malt extract, peptone, NZ amine, and potatoes, carbon sources such as glucose, maltose, sucrose, starch, and organic acids, nitrogen sources such as ammonium sulfate, urea, and ammonium chloride, inorganic nutrient sources such as phosphate salts, magnesium, potassium, and iron, and vitamins, may be used in appropriate combinations.

In the cultivation of a transformant transformed with the expression vector that includes a selection marker, for example, in cases in which the selection marker is a drug-resistant selection marker, a medium that contains a drug corresponding to the drug-resistant selection marker is used, whereas, in cases in which the selection marker is an auxotrophic selection marker, a medium that does not contain a nutrient corresponding to the auxotrophic selection marker is used. The pH of the medium may be selected within a range of from pH 4 to pH 8.

The cultivation may be performed by culturing the transformant in a liquid medium that contains the medium described above, using an ordinary culture method such as shaking culture, aeration-stirring culture, continuous culture, or fed-batch culture.

Culture conditions may be selected, as appropriate, in accordance with the type of transformant, the type of medium, and the type of culture method. The culture conditions should enable the transformant to grow and produce the mutant xylanase according to the invention, and the culture conditions are not particularly limited in other respects.

The culture temperature is from 20° C. to 45° C., and preferably from 24° C. to 37° C., and the cultivation is performed aerobically.

The culture period may be set to a period in the range of from 1 day to 7 days, and the cultivation may be continued until the content of the protein having the desired mutant xylanase activity reaches the maximum.

B. Mutant Xylanase Recovery Process

The mutant xylanase recovery process is a process of recovering the mutant xylanase from at least one of the cultured transformant or a culture product of the transformant.

The method for recovering the mutant xylanase according to the invention after culturing the transformant obtained by transformation may be a method commonly used in the art.

In cases in which the mutant xylanase according to the invention is secreted to outside the transformant obtained by transformation, a crude enzyme solution can be easily obtained by subjecting the culture product of the transformant to centrifugation, filtration, or the like. In cases in which the mutant xylanase according to the invention is accumulated in the transformant obtained by transformation, a crude enzyme solution may be recovered by recovering the cultured transformant using a means such as centrifugation, suspending the recovered transformant in a buffer solution, and breaking the cell membrane of the transformant using a known method such as lysozyme treatment, freezing and thawing, or ultrasonic disintegration.

The crude enzyme solution can be used as a concentrated enzyme by being concentrated by an ultrafiltration method or the like and supplemented with a preservative or the like. A powder enzyme of the mutant xylanase can be obtained by using, for example, a spray-drying method after the concentration.

In cases in which the recovered crude enzyme solution having a xylanase activity needs to be separated and purified, for example, salting-out using ammonium sulfate or the like, organic solvent precipitation methods using alcohol or the like, membrane separation methods using dialysis, ultrafiltration or the like, and known chromatographic separation methods such as ion-exchanger chromatography, reversed-phase high-speed chromatography, affinity chromatography, and gel filtration chromatography, may be performed in appropriate combinations.

(4) USE OF MUTANT XYLANASE

As described above, the mutant xylanase according to the invention has stable activity over a long period of time even under conditions in which enzymes easily inactivate. Therefore, the mutant xylanase according to the invention can be used in a wide range of uses.

A composition according to the invention includes the mutant xylanase described above, and may also include freely-selected components suitable for the desired application, if necessary.

The composition according to the invention includes the mutant xylanase described above, which works stably over a long period of time even under conditions in which enzymes easily inactivate. Therefore, the composition according to the invention can be used for various uses.

The content of the mutant xylanase may be set, as appropriate, in accordance with the use of the composition, and is not particularly limited.

The mutant xylanase according to the invention can be used in various uses. The mutant xylanase is preferably utilized in the manner described below.

[Method of Producing Saccharide from Lignocellulosic Raw Material]

The method of producing a saccharified product of lignocellulose according to the invention includes contacting the mutant xylanase with a lignocellulosic raw material.

In the method of producing a saccharified product of lignocellulose according to the invention, the mutant xylanase described above, which is able to work stably over a long period of time even under a condition in which enzymes easily inactivate, is used; therefore, the production can be performed under conditions in which enzymes easily inactivate, and saccharification of lignocellulose can be efficiently achieved.

Known lignocellulosic raw materials having a low lignin content may be used as the lignocellulosic raw material.

The phrase "low lignin content" refers to a lignin content of lower than 30% by mass, considering that the average lignin content of lignocellulosic raw materials is about 30% by mass with respect to the total amount of lignocellulosic raw material. Lignocellulosic raw materials having a lignin content of 20% by mass or lower are preferable, and lignocellulosic raw materials having a lignin content of 10% by mass or lower are more preferable.

Examples of the lignocellulosic raw material include pulp fibers that include cellulose and hemicellulose as main components, and that are obtained by high-degree removal of lignin from lignocellulosic materials such as softwood, hardwood, a logging residue, construction waste wood, pruning waste, sawdust, kenaf, and agricultural wastes such as rice straw and wheat straw using a chemical pulp production method such as alkali extraction or alkaline digestion or using a method such as organosolve. Preferable examples thereof include hardwood kraft pulp, softwood kraft pulp, mechanical pulp, pulp derived from a herbaceous plant such as kenaf, wastepaper or paper sludge (including pulp fiber content recovered from a paper pulp mill), or any mixture thereof. In particular, hardwood kraft pulp and softwood kraft pulp are more preferable.

Each of these lignocellulosic raw materials is available from general pulp manufacturing companies.

Examples of methods for contacting the mutant xylanase with a lignocellulosic raw material include: a method including adding the mutant xylanase to the lignocellulosic raw material and allowing the reaction to proceed while stirring; a method including allowing the reaction to proceed while shaking; and a method including sufficiently mixing the mutant xylanase and the lignocellulose and then allowing the mixture to stand still so as to allow the reaction to proceed. From the viewpoint of reaction efficiency, a preferable method is a method including adding the mutant xylanase to a lignocellulosic raw material and allowing the reaction to proceed while stirring.

Reaction vessels usable for the reaction are not particularly limited. The reaction vessel is preferably a reaction vessel capable of stirring so as to sufficiently mix the lignocellulosic raw material and the mutant xylanase that have been added thereinto, and having a temperature control function with which the temperature can be maintained at the optimum temperature of the mutant xylanase.

The reaction temperature may be any temperature at which the mutant xylanase can work, without particular restrictions. For example, the reaction temperature may be from 40° C. to 60° C., and preferably from 40° C. to 55° C.

The pH of the solution in the saccharification reaction vessel may be any pH at which the mutant xylanase can work, without particular restrictions. For example, the pH may be from pH 4 to pH 7, and preferably from pH 4 to pH 6.

In the method of producing a saccharified product of lignocellulose according to the invention, in addition to the mutant xylanase according to the invention, other enzymes may be used in combination with the mutant xylanase, if necessary.

In regard to the other enzymes, enzymes, for example, cellulase, xylosidase, mannanase, pectinase, galactosidase, glucuronidase, and arabinofuranosidase, may be used in combination with the mutant xylanase. From the viewpoint of efficient production of a saccharified product of lignocellulose, cellulase is preferably used in combination with the mutant xylanase.

Known cellulases that decompose cellulose into glucose may be used as the cellulase, without restrictions. Examples of the cellulase include cellulases having at least one activity selected from an endoglucanase activity, a cellobiohydrolase activity, or a β-glucosidase activity. In addition, from the viewpoint of enzymatic activity, the cellulase is preferably an enzyme mixture having these activities.

The origin of the cellulase is not limited, and cellulases of filamentous fungi, Basidiomycetes, bacteria, and the like may be used. For example, it is possible to use one, or a mixture of two or more, selected from the group consisting of: cellulases derived from various sources such as filamentous fungi of the genus *Trichoderma*, the genus *Acremonium*, the genus *Aspergillus* or the like, basidiomycetes of the genus *Irpex* or the like, bacteria of the genus *Aeromonas*, the genus *Clostridium*, the genus *Bacillus*, the genus *Pseudomonas*, the genus *Penicillium*, the genus *Humicola*, or the like; and cellulases produced by genetic recombination using cellulases derived from these sources as templates. It is also possible to directly use a cellulase formulation available in the general market, a cultured product of any of the microorganisms mentioned above, or a filtrate obtained from the cultured product.

Among these, cellulase derived from the genus *Trichoderma* or cellulase derived from the genus *Acremonium* is preferable in consideration of their strong cellulose-decomposing power.

Examples of commercially available cellulases that can be used include ACCELLERASE 1000 (manufactured by Genencor Co., Ltd.), ACCELLERASE 1500 (manufactured by Genencor), ACCELLERASE XC (manufactured by Genencor), ACCELLERASE XY (manufactured by Genencor), ACCELLERASE DUET (manufactured by Genencor), ACCELLERASE TRIO (manufactured by Genencor), CELLUCLAST (manufactured by Novozymes), CELLIC CTEC (manufactured by Novozymes), CELLIC HTEC (manufactured by Novozymes), CELLIC CTEC2 (manufactured by Novozymes), CELLIC HTEC2 (manufactured by Novozymes), *ACREMONIUM* CELLULASE (manufactured by Meiji Seika Pharma Co., Ltd.), MEICELLASE (manufactured by Meiji Seika Pharma Co., Ltd.), CELLULASE AMANO A (manufactured by Amano Enzyme Co., Ltd.), CELLULASE AMANO T (manufactured by Amano Enzyme Co., Ltd.), CELLULASE DAIWA (manufactured by Daiwa Fine Chemicals Co., Ltd.), CELLULIZER (manufactured by Nagase Biochemicals Ltd.), DRISELASE (manufactured by Kyowa Hakko Kogyo Co., Ltd.), CELLULASE ONOZUKA (manufactured by Yakult Pharmaceutical Industry Co., Ltd.), and CELLULOSIN (manufactured by Hankyu Bioindustry Co., Ltd.).

The mixing ratio of the mutant xylanase to cellulase may be any mixing ratio at which the production amount of reducing sugar is maximized. Preferably, the mutant xylanase is mixed in a ratio of from 20% to 60% with respect to cellulase.

The concentration of lignocellulosic raw material as a substrate to be added into the reaction vessel and the total concentration of enzymes including the mutant xylanase and the other enzymes (hereinafter referred to as simply "enzymes") are not particularly limited.

For operations such as the transfer, charging, and the like of lignocellulosic raw material, a solid content concentration of from 8% to 30% by mass is preferable.

The enzymes to be used may be added in an amount sufficient for efficient decomposition of the substrate in view of the activity of the enzymes. The amount of the enzymes may be adjusted, as appropriate, in accordance with, for example, the types of the enzymes.

The saccharified product produced by the method of producing a saccharified product from a lignocellulosic raw material according to the invention and the method of producing a saccharified product from a lignocellulosic raw material involving reutilization of saccharification enzymes according to the invention may be any saccharified product derived from lignocellulose. Specific examples of the saccharified product include monosaccharides, and oligosaccharides, which consist of two or more sugar units. Examples of the monosaccharides include glucose, xylose, arabinose, fructose, mannose, and galactose.

The saccharified product may be used to produce chemicals, fuels, plastics, and other products or intermediates. The saccharified product may also be used as a raw material for fermentation for producing these substances using microorganisms.

Examples of the chemicals, fuels, plastics, and other products include ethanol, isopropanol, acetone, acetate, 1,3- propanediol, butanediol, glycerol, ethylene glycol, amino acids, organic acids, furfural, polyhydroxyalkanoates, animal feeds, and xylose.

In particular, the saccharified product is highly suitable for use in fermentative production of ethanol, isopropanol, lactic acid, or the like.

[Method of Producing Mutant Xylanase for Reutilization]

The method of producing a mutant xylanase for reutilization according to the invention includes recovering the mutant xylanase according to the invention from a saccharification reaction solution that contains a saccharified product of lignocellulose obtained by the method of producing a saccharified product of lignocellulose; this process is hereinafter also referred to as a "recovery process", and the saccharification reaction solution mentioned above is hereinafter also referred to as simply the "saccharification reaction solution".

According to this method, the mutant xylanase according to the invention can be produced at low cost.

In the recovery process, the recovery method to be used may be a known method. Examples thereof include a method including performing solid-liquid separation, and recovering the enzyme using a membrane device or other known device capable of recovering the enzyme.

Examples of methods for solid-liquid separation include centrifugation or coarse filtration of the saccharification reaction solution.

With regard to the conditions for the centrifugation or coarse filtration, methods usually employed in the art may be used as they are. For example, in the case of centrifugation, can be performed at from 500×g to 10000×g.

In the case of coarse filtration, filtration may be performed using a stainless steel filter, a ceramic filter, or a resin filter membrane, each of which has an aperture size of from 0.1 μm to 2 mm.

Microfiltration using a microfiltration membrane may be performed. In this case, microfiltration membranes having an average pore size of from 0.01 μm to 10 μm are preferably used.

Examples of methods for microfiltration using a microfiltration membrane include pressure filtration, vacuum filtration, cross-flow filtration, and centrifugal filtration. Among them, cross-flow filtration enables reduction of membrane fouling.

In the case of recovering enzymes from a solution after solid-liquid separation, examples of methods therefore include a method in which a resin column is used and a method in which a membrane device is used.

Examples of the method in which a resin column is used include known chromatographic separation methods such as ion exchanger chromatography, reversed-phase high speed chromatography, affinity chromatography, and gel filtration chromatography.

In regard to the membrane device, recovery may be performed using, for example, a membrane device having an ultrafiltration membrane, a dialysis membrane, or the like. Among them, use of an ultrafiltration membrane having an average pore size of from 0.001 μm to 0.01 μm is more preferable.

There are ultrafiltration membranes of, for example, flat membrane type, multistage flat membrane type, and hollow fiber type. The ultrafiltration described above may be any of these types. In the case of the flat membrane type, an appropriate filtration speed can be achieved by applying a pressure to the inside of the reaction tank. Nitrogen gas, helium gas, air, or the like is preferably employed for the application of a pressure. It is preferable to install an impeller in the reaction tank in accordance with the necessity. Stirring of the liquid using an impeller prevents fouling on the membrane surface, and enables maintenance of a more favorable filtration speed. In the cases of the multistage flat membrane type and the hollow fiber type, liquid may be supplied from a substrate supply tank to the reaction tank using a pump, whereby an appropriate filtration pressure and an appropriate linear velocity are maintained, and a more favorable filtration speed can be maintained.

Examples of filtration methods include an immersed membrane method, an ultrafiltration method, and a microfiltration method. Pressure filtration, vacuum filtration, cross-flow filtration, centrifugal filtration, and the like are usable in both of the ultrafiltration method and the microfiltration method. Filtration operations are roughly classified into constant pressure filtration, constant flow filtration, and filtration with a non-constant pressure and a non-constant flow; there are no particular limitations on the filtration operations in the invention.

Examples of the material of the membrane used in the recovery process in the invention include cellulose acetate, aromatic polyamide, polyvinyl alcohol, polysulfone, polyvinylidene fluoride, polyethylene, polyacrylonitrile, ceramic, polypropylene, polycarbonate, and polytetrafluoroethylene (TEFLON (registered trademark)). Among these materials, it is more preferable to use a membrane made of an acid-resistant non-cellulosic material, such as polyacrylonitrile or polysulfone, in consideration of use of a cellulase and reaction under acidic conditions.

The saccharification reaction solution immediately after production thereof may be used as the saccharification reaction solution for use in the recovery process, without any pretreatment such as the solid-liquid separation.

A mutant xylanase for reutilization produced by the method of producing a mutant xylanase for reutilization according to the invention may be used in various uses, as in the case of the mutant xylanase according to the invention described above. The mutant xylanase for reutilization is also usable for the method of producing a monosaccharide described below.

[Method of Producing Monosaccharide]

A method of producing a monosaccharide according to the invention includes:

recovering the mutant xylanase according to the invention from a saccharification reaction solution containing a saccharified product of lignocellulose obtained by the method of producing a saccharified product of lignocellulose described above (the recovering of the mutant xylanase is hereinafter also referred to as the "recovery process", and the saccharification reaction solution mentioned above is hereinafter also referred to as simply the "saccharification reaction solution"); and producing a monosaccharide by contacting the recovered mutant xylanase with a lignocellulosic raw material (hereinafter referred to as simply the "re-saccharification process").

In this way, the mutant xylanase according to the invention can effectively be utilized.

To this recovery process, the recovery process described above is applied.

In the re-saccharification process, the lignocellulosic raw material and water are added to the enzyme solution containing the recovered mutant xylanase, and a re-saccharification reaction is performed with stirring while controlling the pH and the temperature. The conditions of the pH and the reaction temperature may be the same as those described in the explanation of the method of producing a saccharified product from a lignocellulosic raw material.

In the re-saccharification process, in addition to the lignocellulosic raw material and water to be additionally fed, a solid obtained by the solid-liquid separation in the recovery process is preferably added. This makes it possible to effectively utilize unreacted lignocellulose contained in the solid as a result of the solid-liquid separation using a membrane device or a resin column, and the mutant xylanase that is adsorbed on the unreacted lignocellulose.

In the re-saccharification process according to the invention, either the mutant xylanase or the solid product obtained as a result of the solid-separation, or both may be additionally fed.

In the method of producing a monosaccharide according to the invention, the recovery process and the re-saccharification process may be performed repeatedly. This makes it possible to reduce the cost for catalyst over a period of time during which the activity of the recovered mutant xylanase is maintained.

In the method of producing a monosaccharide according to the invention, in cases in which the recovery process and the re-saccharification process are repeated, the mutant xylanase according to the invention may be newly added for the re-saccharification process. The amount of the mutant xylanase to be newly added is not particularly limited, and is preferably no more than 50% by mass of the amount of the mutant xylanase used in the initial saccharification reaction, from the economical viewpoint. The amount of the mutant xylanase to be newly added is more preferably no more than 20% by mass of the amount of the mutant xylanase used in the initial saccharification reaction from the economical viewpoint, and the amount of the mutant xylanase to be newly added is still more preferably no more than 10% by mass of the amount of the mutant xylanase used in the initial saccharification reaction.

The monosaccharide produced by the method of producing a monosaccharide according to the invention may be any monosaccharide derived from lignocellulose. Specific examples thereof include glucose, xylose, arabinose, fructose, mannose, and galactose.

[Method of Bleaching Pulp]

A method of bleaching a pulp according to the invention includes contacting the mutant xylanase with a pulp.

In the method of bleaching a pulp according to the invention, the mutant xylanase described above, which stably works over a long period of time even under a condition in which enzymes easily inactivate, is used, and, therefore, the bleaching can be performed under a condition in which enzymes generally easily inactivate, and pulp can be bleached with high efficiency.

The pulp used in the process of contacting the mutant xylanase with a pulp may be a wood pulp or a non-wood pulp. Examples of the wood pulp include those made from softwood or hardwood raw materials. Examples of the non-wood pulp include those made from raw materials such as bagasse, which is a cane trash of sugar cane left after squeezing, straw, hemp, and cotton. Further examples of the non-wood pulp include waste paper pulp made from waste paper, such as newspaper or magazine.

These pulps are roughly classified into mechanical pulps obtained by extracting fibers from a raw material using a physical force and chemical pulps obtained by extracting fibers by chemical treatment. Examples of mechanical pulps include ground pulp, refiner ground pulp, thermomechanical pulp, and chemi-thermo-mechanical pulp. Examples of chemical pulps include kraft pulp, alkaline pulp, and sulfite pulp.

In the process of contacting the mutant xylanase with a pulp, in addition to the mutant xylanase, another hemicellulase or ligninase may additionally be used. This heightens the degree of pulp bleaching.

The origins of the hemicellulase and the ligninase are not particularly limited, and examples of the origins include filamentous fungi, basidiomycetes, and bacteria.

The method of bleaching a pulp according to the invention preferably further includes a delignification treatment process and a bleaching process, in addition to the process of contacting the mutant xylanase with a pulp.

In the present specification, the delignification treatment process may be any method that aims to positively remove lignin from a pulp, and methods that have been practiced from the past may be used. Examples thereof include a method described in JP-A No. 2004-263310.

In the present specification, the bleaching process may be any process performs bleaching treatment on the pulp, and the scope thereof generally encompasses process aiming at, for example, removal of lignin remaining in the pulp or improvement in the whiteness of the pulp. The bleaching process is a process that follows the delignification treatment process, and methods that have been practiced from the past may be used. Examples thereof include a method described in JP-A No. 2010-1594.

In cases in which the process of contacting the mutant xylanase according to the invention with a pulp is performed in combination with the delignification treatment process and the bleaching process, the process of contacting the mutant xylanase with a pulp may be performed at any point in time during processes from the delignification treatment process to the bleaching process. Specifically, the process of contacting the mutant xylanase with a pulp may be performed before or after the delignification treatment process, or before or after the bleaching process. Alternatively, the process of contacting the mutant xylanase with a pulp may be performed simultaneously with the delignification treatment process or the bleaching process.

Preferably, the process of contacting the mutant xylanase according to the invention with a pulp is performed as a part of the bleaching process. In particular, from the viewpoint of enabling the ability of the mutant xylanase according to the invention to be maximally exerted, the process of contacting the mutant xylanase with a pulp is more preferably performed at a stage of the bleaching process at which the lignin content is small.

Alternatively, the process of contacting the mutant xylanase with a pulp may also be used, for example, as a part of the bleaching process in which, from among bleaching processes described above, chemical bleaching is performed using chlorine, chlorine dioxide, nitrogen dioxide, a hypochlorite, oxygen, hydrogen peroxide, ozone, or the like.

[Detergent]

A detergent according to the invention includes the mutant xylanase described above, and may further include other components, as necessary.

The detergent according to the invention has improved performance due to inclusion of the mutant xylanase, which exhibits stable activity even under severe conditions in which enzymes easily inactivate.

The scope of the detergent according to the invention encompasses various detergents such as laundry detergents and detergents for automatic dishwashers. The detergent according to the invention may be used as detergents for home use and industrial use. The detergent according to the invention is also usable as a modifier for fiber products for clothing.

When the detergent according to the invention is used as a modifier for a fiber product for clothing, the fiber product for clothing to which the detergent is applied may be, for example, cotton fibers, hemp fibers, or cellulose-containing fibers such as rayon or tencel.

The detergent according to the invention may further include other enzymes in addition to the mutant xylanase, in accordance with the uses. Enzymes known in the art may be used as the other enzymes. Examples thereof include protease, cellulase, amylase, and lipase. The origins of the other enzymes are not limited, and examples thereof include filamentous fungi, basidiomycetes, and bacteria.

The detergent according to the invention may also include components, other than the other enzymes mentioned above, that are usually used in detergents, examples of which include surfactants, cleaning aids, bleaching agents, and fluorescent agents.

Examples of the surfactant include anionic surfactants, nonionic surfactants, amphoteric surfactants, and cationic surfactants. Anionic surfactants and nonionic surfactants are preferable.

Examples of the anionic surfactants include sodium salts of fatty acids (soap), sodium α-sulfonated fatty acid ester, sodium linear alkyl benzene sulfonate (LAS), sodium alkyl sulfate (AS), sodium alkyl ether sulfate (AES), sodium α-olefin sulfonate (AOS), and sodium alkyl sulfonate.

Examples of the nonionic surfactants include polyoxyalkylene alkyl ether (AE), polyoxyethylene alkyl phenyl ether (APE), sucrose fatty acid salt esters, sorbitan fatty acid esters, polyoxyethylene sorbitan fatty acid esters, polyoxyethylene fatty acid esters, and alkanol amides.

Examples of the cleaning aids include alkali buffers, divalent metal ion scavengers, and anti-redeposition agents. Specific examples thereof include polyphosphates such as tripolyphosphate and pyrophosphate, aluminosilicates such as A-type zeolite, carbonates such as sodium carbonate, sodium sesquicarbonate, and sodium hydrogen carbonate, polymers such as polyethylene glycol, carboxylic acid-based polymers, polyvinyl alcohol, polyvinyl pyrrolidone, and polyglycidyl acid salts, cellulose derivatives such as carboxymethyl cellulose, and aminocarboxylic acid-based polymers such as polyaspartic acid.

Examples of the bleaching agents include sodium hypochlorite, dichloroisocyanurates, sodium chlorite, hydrogen peroxide, sodium percarbonate, sodium perborate, peracetic acid, hydrosulfite, and thiouric acid dioxide.

Examples of the fluorescent agents include bis-(triazinylamino)stilbene disulfonic acid derivatives and bis-styryl biphenyl derivatives.

The detergent according to the invention may be combined with the surfactant, the cleaning aid, the bleaching agent, the fluorescent agent, or the like, and produced according to ordinary methods.

The form of the detergent may be selected in accordance with the uses, and may be, for example, liquid, powder, granules, paste, or solid.

[Animal Feed]

An animal feed according to the invention includes the mutant xylanase described above, and may further include other components, as necessary.

The animal feed according to the invention includes the mutant xylanase that exhibits stable activity even under severe conditions in which enzymes easily inactivate. As a result, the absorption efficiency of plant nutrients in animals that have eaten the animal feed according to the invention is improved, and the digestibility thereof in the stomach of the animals is also improved, due to the decomposition of plant fibers abundant in the animal feed.

The content of the mutant xylanase in the animal feed according to the invention should be an amount capable of improving the digestibility of the animal feed in the stomach of animals, but the content is not particularly limited in other respects.

Examples of the animal feed include xylan-containing ready-made animal feeds, and grains. Among the grains, wheat, corn, rye, barley, oats, triticale, rice, and sorghum are particularly preferable.

The mutant xylanase in the animal feed according to the invention may be used in combination with other feed additives and/or other enzymes.

Examples of other feed additives include vitamin feed additives, mineral feed additives, amino acid feed additives, and permeable protective agents.

Examples of other enzymes include cellulase, amylase, and protease. The origins of these enzymes are not limited, and enzymes derived from filamentous fungi, basidiomycetes, bacteria, or the like may be used.

The animal feed according to the invention is usable for a wide range of animals. Preferable examples of the animals include poultry such as chickens, turkeys, ducks, and geese, ruminants such as cows, horses, and sheep, boars and pigs such as pigs, rodents such as rabbits, and fishes.

The animal feed according to the invention may be produced by any method as long as the animal feed includes the mutant xylanase, and the method for producing the animal feed is not particularly limited. Addition of the mutant xylanase into animal feed may be performed at any stage selected from before the production of the animal feed, during the production of the animal feed, or at the final stage of the production of the animal feed. The mutant xylanase may be directly added to a ready-made animal feed that has been formed into a pellet form or a mash form. Alternatively, the mutant xylanase may be incorporated into an animal feed by being directly added into drinking water.

[Bread-Making Modifier]

A bread-making modifier according to the invention includes the mutant xylanase described above, and may further include other components, as necessary.

The bread-making modifier according to the invention includes the mutant xylanase described above, which exhibits stable activity even under severe conditions in which enzymes easily inactivate. Due to the inclusion of the mutant xylanase, the bread-making modifier according to the invention exhibits stable activity even during the fermentation process in bread making, which is carried out at from 35° C. to 40° C. for from 1 hour to 2 hours, whereby hemicellulose contained in the flour can be decomposed, and the quality of bread making can be modified.

The bread-making modifier according to the invention may include other bread-making modifiers, in addition to the mutant xylanase. Examples of the other bread-making modifiers include monoglycerides, organic acid monoglycerides, glycerin fatty acid esters, propylene glycol fatty acid esters, sorbitan fatty acid esters, phospholipids, ascorbic acids and derivatives thereof, organic acids, amino acids, and salts.

In regard to the type of bread to which the bread-making modifier according to the invention is to be added, the bread may be any bread that is produced by mixing ingredients for the bread and further performing kneading, fermentation, baking, and the like. Examples thereof include, besides white bread, special bread, stuffed bread, sweet bun, steamed bread, pancakes, and doughnuts.

Examples of ingredients for these breads include flour, water contents such as water and dairy products, yeast, sugars, common salt, and oils and fats (such as shortening, lard, margarine, butter, and liquid oil). If necessary, eggs, seasonings (such as glutamic acids and nucleic acids), baking powder, flavors, or the like may also be added. In cases in which flour is a main raw material, rye flour, rice flour, or the like may also be used in combination with the flour. In the present specification, the term "dough" means a material obtained by mixing and kneading the bread ingredients mentioned above.

Methods for producing bread may be commonly-employed methods that include a fermentation process, without particular limitations. For example, a straight dough method, a sponge and dough method, and a pre-ferment and dough method may be used.

For the fermentation process, commonly-employed methods may be used. The fermentation process is preferably performed at from 35° C. to 40° C. for from 1 hour to 2 hours since the fermentation time can be shortened by setting the fermentation temperature relatively high as compared to room temperature.

The bread-making modifier according to the invention may be, for example, mixed as powder with a raw material such as flour, or dissolved in water before use, or added as powder or liquid at a certain stage in the process.

Although embodiments of the invention are described above, these embodiments are merely examples of the invention, and various configurations, other than those described above, may also be employed.

EXAMPLES

The invention will be described in more detail with reference to the following Examples. However, the invention is by no means limited to the examples below. The percentages indicating the amounts of components included in the compositions in the examples are percentages by mass, unless otherwise specified.

Example 1

Method for Measuring Xylanase Activity (Standard Assay)

The amount of reducing sugars released by the hydrolysis of xylan was measured by the DNS method (Bailey et al., 1992), to determine xylanase activity.

The substrate used for evaluation was a supernatant prepared by vigorously mixing together a 100 mM sodium citrate buffer solution (pH 4.5) with 1% (w/w) birchwood xylan (manufactured by Sigma-Aldrich Corporation) and then centrifuging at 5,000×g for 15 minutes.

Xylanase was mixed with this substrate solution such that the amount of xylanase was 0.1% (w/w) of that of the substrate solution, and a reaction was allowed to proceed with stirring at 45° C. for 30 minutes. The amount of reducing sugars in the resulting reaction solution was measured, to determine the xylanase activity.

Example 2

Production of Xylanase Mutant by Site-Directed Mutagenesis and Evaluation Thereof (1) Construction of Expression Vectors: YEp-GAPDHp-GAs-TVX and YEp-GAPDHp-GAs-ACX (a) Obtainment of Promoter Sequence Using a genomic DNA sequence of *Saccharomyces cerevisiae* as a template, a promoter sequence (GenBank Accession Number: A35397.1) of glyceraldehyde-3-phosphate dehydrogenase (hereinafter referred to as "GAPDH") was obtained by PCR. The primer sequences used in the PCR are presented as SEQ ID Nos. 55 and 56 in Table 4 below.

(b) Obtainment of Signal Sequence

Using a genomic DNA sequence of *Rhizopus oryzae* as a template, a signal sequence of a glucoamylase gene (GenBank Accession Number: D00049.1) was obtained by PCR. The primer sequences used in the PCR are presented as SEQ ID NOs. 57 and 58 in Table 4 below.

(c) Ligation of Promoter Sequence and Signal Sequence

The DNA sequences amplified by the PCR were purified using a phenol/chloroform solution, and recovered through ethanol precipitation. The purified promoter sequence and signal sequence were digested with a restriction enzyme BglII, and thereafter individually subjected to agarose electrophoresis, and fragments that included desired DNAs were separated and purified. The fragments thus obtained were ligated using a DNA ligase (manufactured by Takara Shuzo Co., Ltd). The ligated product is hereinafter abbreviated to "GAPDHp-GAs".

(d) Amplification of *T. Viride*-Derived Xylanase II Gene

Using a genomic DNA sequence of *T. viride* as a template, the full length of a *T. viride*-derived xylanase II gene (a base sequence encoding the xylanase gene as well as a secretory signal sequence) was obtained by PCR. The primer sequences used in the PCR are presented as SEQ ID NO: 59 and SEQ ID NO 60 in Table 4 below. The obtained sequence is presented as SEQ ID NO: 74 in the Sequence Listing.

(e) Amplification of *A. Cellulolyticus*-Derived Xylanase Gene

Using a genomic DNA sequence of *A. cellulolyticus* as a template, the full length of an *A. cellulolyticus*-derived xylanase gene (a base sequence encoding the xylanase gene as well as a secretory signal sequence) was obtained by PCR. The primer sequences used in the PCR are presented as SEQ ID NOs: 61 and 62 in Table 4 below. The obtained sequence is presented as SEQ ID NO: 75 in the Sequence Listing.

(f) Ligation of Promoter Sequence, Signal Sequence, and Xylanase Gene

Using the *T. viride*-derived xylanase II obtained in (d) as a template, the base sequence encoding the xylanase gene, excluding the signal sequence, was obtained by PCR. The primers used in the PCR are presented as SEQ ID NO: 63 and SEQ ID NO 64 in Table 4 below. Thereafter, the obtained fragment was purified and digested with a restriction enzyme SacI, and then ligated to GAPDHp-GAs fragment. The ligation product is hereinafter abbreviated to "GAPDHp-GAs-TVX".

Similar to the above, also with respect to the *A. cellulolyticus*-derived xylanase I obtained in (e), the gene at the secretory protein portion thereof was obtained by PCR, and, after purification, digested with a restriction enzyme SacI and ligated to GAPDHp-GAs fragment. The ligation product is hereinafter abbreviated to "GAPDHp-GAs-ACX". The primers used in the PCR are presented as SEQ ID NO: 65 and SEQ ID NO 66 in Table 4 below.

Here, the methods for the purification and ligation of DNA fragments in this step are the same as those in the step (c).

(g) Introduction into Expression Vector

The GAPDHp-GAs-TVX fragment and a multicopy expression vector YEp24 (ATCC 7769) for budding yeast were digested with restriction enzymes XmaI and BamHI (the former producing a fragment of about 1.3 kbp and the latter producing a fragment of about 7.4 kbp), and, after purification, ligated to each other to obtain a plasmid for producing a *T. viride*-derived xylanase II mutant (hereinafter abbreviated to YEp-GAPDHp-GAs-TVX). Similar to the above, the fragment GAPDHp-GAs-ACX and YEp24 were digested with the restriction enzymes XmaI and BamHI (the former producing a fragment of about 1.5 kbp and the latter producing a fragment of about 7.4 kbp), and, after purification, ligated to each other to obtain an expression vector for producing an *A. cellulolyticus*-derived xylanase I mutant (hereinafter abbreviated to YEp-GAPDHp-GAs-ACX).

The methods for the purification and ligation of the DNA fragments in this step are the same as those in the step (c). The YEp24 is available from the American Type Culture Collection, which is a bank of cells and microorganisms.

TABLE 4

| SEQ ID NO: 55 | GACTAGCCCGGGTCGAGTTTATCATTATC |
| SEQ ID NO: 56 | GACGAGAGATCTCCATTTTGTTTATTTATGTG |
| SEQ ID NO: 57 | GACTAGAGATCTATGCAACTGTTCAATTTGCC |
| SEQ ID NO: 58 | CAGCATGAGCTCAGCAGAAACCAGCAAAG |
| SEQ ID NO: 59 | ATGGTTTCCTTCACCTCCCTCCTCGCCGGC |
| SEQ ID NO: 60 | TTAGCTGACGGTAATAGAAGCAGAGCCAGA |
| SEQ ID NO: 61 | ATGGGCATCTCATCTATTCTTCTCTCTGCT |
| SEQ ID NO: 62 | CTATTGGCACTGACTGTAGTAAGCGTTAAA |
| SEQ ID NO: 63 | GATTAGGAGCTCCAGACGATTGGTCCCG |
| SEQ ID NO: 64 | GACTAGGGATCCTTAGCTGACGGTAATAG |
| SEQ ID NO: 65 | GATTATGAGCTCGCTGAGGCGATCAACTAC |
| SEQ ID NO: 66 | GATTAGGGATCCCTATTGGCACTGACTGTAG |

(2) Site-Directed Mutagenesis

Mutants used in examples of the invention had mutations introduced using a LA PCR in vitro Mutagenesis Kit manufactured by Takara Shuzo Co., Ltd. and using the expression vectors constructed in step (1) as templates The primers used were synthesized oligonucleotides.

PCR was performed using the expression vector YEp-GAPDHp-GAs-TVX as a template and using SEQ ID NO: 5 and SEQ ID NO 6, SEQ ID NO: 7 and SEQ ID NO 8, SEQ ID NO: 9 and SEQ ID NO 10, and SEQ ID NO: 11 and SEQ ID NO 12, which are given in Table 5 below, as primers, to obtain a mutant xylanase expression vector YEp-GAPDHp-GAs-TVX01.

In addition, using the expression vector YEp-GAPDHp-GAs-ACX as a template and using the sequences of SEQ ID NO: 21 and SEQ ID NO 22, which are given in Table 5 below, as primers, YEp-GAPDHp-GAs-L154M was obtained which had a substitute amino acid residue that was a methionine substituted for a leucine residue at position 154 of SEQ ID NO: 2 in the Sequence Listing.

Similar to the above, YEp-GAPDHp-GAs-ACX01 was obtained using the expression vector YEp-GAPDHp-GAs-ACX as a template and using the sequences of SEQ ID NO: 13 and SEQ ID NO 14, the sequences of SEQ ID NO: 15 and SEQ ID NO 16, the sequences of SEQ ID NO: 17 and SEQ ID NO 18, the sequences of SEQ ID NO: 19 and SEQ ID NO 20, the sequences of SEQ ID NO: 21 and SEQ ID NO 22, the sequences of SEQ ID NO: 23 and SEQ ID NO 24, the sequences of SEQ ID NO: 25 and SEQ ID NO 26, the sequences of SEQ ID NO: 27 and SEQ ID NO 28, and the sequences of SEQ ID NO: 29 and SEQ ID NO 30, which are given in Table 5 below, as primers.

Similar to the above, YEp-GAPDHp-GAs-ACX02 was obtained using the expression vector YEp-GAPDHp-GAs-ACX as a template and using the sequences of SEQ ID NO: 15 and SEQ ID NO 16, the sequences of SEQ ID NO: 21 and SEQ ID NO 22, the sequences of SEQ ID NO: 31 and SEQ ID NO 32, and the sequences of SEQ ID NO: 33 and SEQ ID NO 34, which are given in Table 5 below, as primers.

Similar to the above, YEp-GAPDHp-GAs-ACX03 was obtained using the expression vector YEp-GAPDHp-GAs-ACX as a template and using the sequences of SEQ ID NO: 21 and SEQ ID NO 22, the sequences of SEQ ID NO: 31 and SEQ ID NO 32, the sequences of SEQ ID NO: 35 and SEQ ID NO 36, the sequences of SEQ ID NO: 37 and SEQ ID NO 38, and the sequences of SEQ ID NO: 39 and SEQ ID NO 40, which are given in Table 5 below, as primers.

Competent cells of *Escherichia coli* HB101 (manufactured by Toyobo Co., Ltd.) were transformed with the plasmids that contained mutant xylanases, to obtain transformants.

Plasmids were prepared from the bacterial cells using an alkaline-SDS extraction method, and the base sequences of the xylanase gene portions thereof were determined using a DNA sequencer, as a result of which the introduction of amino acid substitutions in the xylanase gene-encoding region of each of YEp-GAPDHp-GAs-TVX and YEp-GAPDHp-GAs-ACX, which are templates, was confirmed.

TABLE 5

| SEQ ID NO: 5 | GTACACCCTCGGCCCCGGCGGCCAG |
| SEQ ID NO: 6 | CGGGGCCGAGGGTGTACGTCACGCC |
| SEQ ID NO: 7 | CAAGAACAGGGTCATCAACTTCTCG |
| SEQ ID NO: 8 | GATGACCCTGTTCTTGGTGCCGG |
| SEQ ID NO: 9 | CGTGACGTTCACCCTCGGCCCCGGC |
| SEQ ID NO: 10 | CGAGGGTGAACGTCACGCCGCCGTG |
| SEQ ID NO: 11 | CTCGGGCAGCTTTGTCGGCGGCAAG |
| SEQ ID NO: 12 | CGACAAAGCTGCCCGAGTTGGACCAG |
| SEQ ID NO: 13 | CATCAACTACGATACGCAGGGGGAC |
| SEQ ID NO: 14 | CCCTGCGTATCGTAGTTGATGGAG |
| SEQ ID NO: 15 | GATACGCAGAGGGACTTTGTGGTGG |
| SEQ ID NO: 16 | CAAAGTCCCTCTGCGTATCGTAGTTG |
| SEQ ID NO: 17 | GATACCAGTCTGTCGGCACACACAAG |
| SEQ ID NO: 18 | GCCGACAGACTGGTATCCGTCGTG |
| SEQ ID NO: 19 | GATCCGCCGAAGCCCCCGGACGAG |
| SEQ ID NO: 20 | GGGGGCTTCGGCGGATCGAGATGTAC |
| SEQ ID NO: 21 | CAGGCGGGCATGAATCTCGGCACAATG |
| SEQ ID NO: 22 | CCGAGATTCATGCCCGCCTGCGCCC |
| SEQ ID NO: 23 | GCAGCGGCACTGGACAAATCTCGCTC |
| SEQ ID NO: 24 | GATTTGTCCAGTGCCGCTGCCGCTCC |
| SEQ ID NO: 25 | CACGGGTCACACCAGCACGAGCAC |

TABLE 5-continued

| | |
|---|---|
| SEQ ID NO: 26 | GTGCTGGTGTGACCCGTGGGTGTG |
| SEQ ID NO: 27 | GTCACACCAACACGAGCACCGCTCC |
| SEQ ID NO: 28 | GTGCTCGTGTTGGTGTGACCCGTGG |
| SEQ ID NO: 29 | CAATGCGGAGAAATTGGCTGGACCGG |
| SEQ ID NO: 30 | CCAGCCAATTTCTCCGCATTGTCCCC |
| SEQ ID NO: 31 | CTTTCTCCGTCAACTACAATACGC |
| SEQ ID NO: 32 | GTAGTTGACGGAGAAAGAACCCG |
| SEQ ID NO: 33 | GTCAACTACGATACGCAGGGGACTTTG |
| SEQ ID NO: 34 | CCCTGCGTATCGTAGTTGACGGAGAAAG |
| SEQ ID NO: 35 | CTCCTTCACGGCCTCGGGTCGGGTG |
| SEQ ID NO: 36 | CCGAGGCCGTGAAGGAGCCGCTGTAG |
| SEQ ID NO: 37 | CGCTTACCACAGTCAGTGCCAATAG |
| SEQ ID NO: 38 | CACTGACTGTGGTAAGCGTTAAAGTAC |
| SEQ ID NO: 39 | CAGTCAGAGCCAATAGGGATCCTC |
| SEQ ID NO: 40 | CCTATTGGCTCTGACTGTAGTAAGC |

(3) Transformation into Yeast and Production of Mutant Xylanase

Competent cells of *Saccharomyces cerevisiae* BY4741 were transformed with the mutant xylanase-containing expression vectors constructed in step (2) using a FAST-YEAST TRANSFORMATION KIT (G-Biosciences), and cultured on an SD-Ura agar medium (0.67% Yeast-nitrogen base without amino acids (Difco Co., Ltd.), 2% glucose, 0.5% casamino acid, 0.077%-Ura DO Supplement (Clontech Co., Ltd.), 2% agar, and deionized water) at 30° C. for 48 hours. The resultant mutants are listed in Table 6.

TABLE 6

| Name of mutant | SEQ ID NO: | Amino acid No. | Before mutation | After mutation |
|---|---|---|---|---|
| TVX01 | 1 | 27 | Tyr | Phe |
| | 1 | 29 | Asn | Leu |
| | 1 | 44 | Asn | Ser |
| | 1 | 58 | Lys | Arg |
| ACX01 | 2 | 33 | Asn | Asp |
| | 2 | 36 | Gly | Arg |

TABLE 6-continued

| Name of mutant | SEQ ID NO: | Amino acid No. | Before mutation | After mutation |
|---|---|---|---|---|
| | 2 | 90 | Thr | Ser |
| | 2 | 132 | Gln | Arg |
| | 2 | 154 | Leu | Met |
| | 2 | 174 | Ser | Thr |
| | 2 | 195 | Pro | His |
| | 2 | 197 | Ser | Asn |
| | 2 | 217 | Gly | Glu |
| ACX02 | 2 | 30 | Ile | Val |
| | 2 | 33 | Asn | Asp |
| | 2 | 36 | Gly | Arg |
| | 2 | 154 | Leu | Met |
| ACX03 | 2 | 30 | Ile | Val |
| | 2 | 59 | Ser | Thr |
| | 2 | 154 | Leu | Met |
| | 2 | 239 | Tyr | His |
| | 2 | 242 | Cys | Ser |

(4) Evaluation of Stability of Mutant Xylanases

The obtained colony was inoculated into an SD-Ura liquid medium (the medium composition being the same as the above-mentioned medium composition except that glucose content was 4%, that the agar was not contained, and that the SD-Ura medium was a liquid medium), and was subjected to pre-cultivation at 30° C. for 24 hours. Thereafter, the resultant pre-culture was inoculated in an amount of 2%, and subjected to main cultivation for 48 hours. Then, the supernatant, which contained the mutant xylanase, was centrifuged, and then subjected to heating treatment at from 50° C. to 55° C., and residual activity of the enzyme was measured according to the measurement method described in Example 1.

<TVX01>

The mutant xylanase produced by the method described in step (2) in Example 2 was subjected to heat treatment at 50° C. for a length of time varied from 0 hour to 72 hours, and then measured with respect to the residual activity thereof using the measurement method described in Example 1. The results are given in Table 7. The symbol WT represents wild type, and the symbols F, L, S, and R respectively represent, in the amino acid sequence of SEQ ID NO: 1 in the Sequence Listing, substitution of a tyrosine residue at position 27 with phenylalanine, substitution of an asparagine residue at position 29 with a leucine residue, substitution of an asparagine residue at position 44 with a serine residue, and substitution of a lysine residue at position 58 with an arginine residue. For the production of a mutant xylanase (Table 7 (e)) in which a tyrosine residue at position 27 was substituted with a phenylalanine residue, primers of SEQ ID NO: 41 and SEQ ID NO 42 given in Table 8 were used.

TABLE 7

| | Name of | Initial Rate of Reaction Before Heat Treatment | Residual Activity [%] | | | |
|---|---|---|---|---|---|---|
| No. | Xylanase | (Relative to WT) | 0 hours | 24 hours | 48 hours | 72 hours |
| (a) | WT | 1.00 | 100% | 0% | 0% | 0% |
| (b) | FLSR (TVX01) | 0.70 | 100% | 97% | 86% | 75% |
| (c) | FLR | 0.48 | 100% | 84% | 74% | 55% |
| (d) | LR | 0.66 | 100% | 0% | 0% | 0% |
| (e) | F | 0.79 | 100% | 0% | 0% | 0% |
| (f) | L | 0.57 | 100% | 0% | 0% | 0% |
| (g) | S | 0.99 | 100% | 0% | 0% | 0% |
| (h) | R | 0.96 | 100% | 0% | 0% | 0% |

TABLE 8

| SEQ ID NO: 41 | CGTGACGTTCACCAATGGCCCCGGC |
|---|---|
| SEQ ID NO: 42 | CATTGGTGAACGTCACGCCGCCGTG |

The mutant xylanases in which a specific amino acid residue or specific amino acid residues were replaced by substitute amino acid residues that are believed to provide stabilization against heat and described in WO 2007/115391 pamphlet, WO 2001/27252 pamphlet, and WO 2005/108565 pamphlet completely inactivated after 24 hours, as demonstrated in rows (d), (f), and (h) in Table 7.

In addition, as shown in rows (e) and (g) in Table 7, the mutant xylanase having a substitute amino acid residue that is a phenylalanine residue substituted for a tyrosine residue at position 27 or the mutant xylanase having a substitute amino acid residue that is a serine residue substituted for an asparagine residue at position 44 also completely inactivated after 24 hours.

However, in the case of the mutant xylanase having substitute amino acid residues that are a leucine residue substituted for an asparagine residue at position 29 and an arginine residue substituted for a lysine residue at position 58 (row (d) in Table 7), further substitution of a tyrosine residue at position 27 with a phenylalanine residue resulted in improvement of residual activity by and provision of a residual activity of 50% or higher even after 72 hours (row (c) in Table 7).

Furthermore, substitution of an asparagine residue at position 44 in this mutant xylanase with a serine residue resulted in provision of an activity close to that of the wild type (row (a) in Table 7) and a residual activity of 70% even after 72 hours (row (b) in Table 7).

asparagine residue at position 151 with a serine residue, substitution of a serine residue at position 161 with a leucine residue, or substitution of a serine residue at position 186 with a threonine residue.

<L154M>

Using the method described in step (3) in Example 2, yeast was transformed with the expression vector that includes a nucleic acid represented by the base sequence encoding the amino acid sequence of a mutant xylanase, and that was produced by the method described in step (2) in Example 2. The yeast that produces the mutant xylanase was subjected to cultivation in liquid. The supernatant of the culture solution was subjected to heat treatment at 50° C. for 24 hours, and then residual activity was measured by the measurement method described in Example 1.

The residual activity of the mutant xylanase was 50%. The mutant xylanase also exhibited an initial rate of reaction before heat treatment that is 1.13 times that of the wild type.

<ACX01, ACX02, and ACX03>

Using the method described in step (3) in Example 2, yeast was transformed with the expression vector that includes a nucleic acid represented by the base sequence encoding the amino acid sequence of a mutant xylanase, and that was produced by the method described in step (2) in Example 2. The yeast that produces the mutant xylanase was subjected to cultivation in liquid. The supernatant of the culture solution was subjected to heat treatment at 50° C. for a length of time varied from 0 to 48 hours, and then residual activity was measured by the measurement method described in Example 1. The results are given in Table 9. In Table 9, WT represents wild type.

The liquid medium used in this process is an SD medium (without Ura) that contained 4% of glucose.

TABLE 9

| No. | Name of Xylanase | Initial Rate of Reaction Before Heat Treatment (Relative to WT) | Residual Activity (%) | | | |
|---|---|---|---|---|---|---|
| | | | 0 hours | 16 hours | 24 hours | 48 hours |
| (i) | WT | 1.00 | 100% | 0% | 0% | 0% |
| (j) | ACX01 | 2.27 | 100% | 89% | 76% | 59% |
| (k) | ACX02 | 0.92 | 100% | 99% | 92% | 66% |
| (l) | ACX03 | 0.80 | 100% | 85% | 79% | 61% |

Many of the mutants that include the four mutation sites according to the invention had properties nearly equivalent to those of TVX01. Specific examples of those mutants include mutants that includes the four mutation sites as well as includes, in the amino acid sequence of SEQ ID NO: 1 in the Sequence Listing, substitution of a glycine residue at position 47 with a cysteine residue, substitution of a glutamine residue at position 52 with a lysine residue, substitution of a valine residue at position 59 with an isoleucine residue, substitution of an asparagine residue at position 67 with an aspartic acid residue, substitution of an asparagine residue at position 69 with an isoleucine residue, substitution of a serine residue at position 80 with an alanine residue, substitution of an asparagine residue at position 97 with an aspartic acid residue, substitution of a leucine residue at position 105 with a methionine residue, substitution of a threonine residue at position 109 with an alanine residue, substitution of a threonine residue at position 120 with an arginine residue, substitution of a threonine residue at position 143 with an isoleucine residue, substitution of an The wild-type *A cellulolyticus*-derived xylanase completely inactivated after heat treatment for 16 hours (row (i) in Table 9). In contrast, the mutant xylanases exhibited an improved residual activity, and the mutant xylanases exhibited a residual activity of 50% or higher even after 48 hours (rows (j), (k), or (l) in Table 9). ACX02 and ACX03 (rows (k) and (l) in Table 9) also exhibited initial rates of reaction before heat treatment that are nearly equivalent to that of the wild-type xylanase, and ACX01 exhibited an activity nearly twice as high as that of the wild-type xylanase (row (j) in Table 9).

Many of the mutants that have all of the mutation sites contained in ACX01 exhibit properties nearly equivalent to those of ACX01. Specific examples of the mutants include a mutant that includes the mutation sites contained in ACX01, and further includes, in the amino acid sequence of SEQ ID NO:3 in the Sequence Listing, substitution of a serine residue at position 133 with an asparagine residue and substitution of a glutamine residue at position 176 with an arginine residue.

Similar to the above, in the case of ACX02, many of the mutants having all of the mutation sites contained in ACX02 exhibit properties nearly equivalent to those of ACX02. Specific examples of the mutants include a mutant that includes the mutation sites contained in ACX02, and further includes, in the amino acid sequence of SEQ ID NO: 3 in the Sequence Listing, substitution of a threonine residue at position 90 with a serine residue, substitution of a glutamine residue at position 132 with an arginine residue, substitution of a serine residue at position 133 with an asparagine residue, substitution of a serine residue at position 174 with a threonine residue, substitution of a proline residue at position 195 with a histidine residue, substitution of a glutamine residue at position 176 with an arginine residue, substitution of a serine residue at position 197 with asparagine residue, and substitution of a glycine residue at position 217 with a glutamic acid residue.

Further, many of the mutants that include all of the mutation sites contained in ACX03 exhibit properties nearly equivalent to those of ACX03. Specific examples of the mutants include a mutant that includes all the mutation sites contained in ACX03, and further includes substitution of a glutamine residue at position 176 in the amino acid sequence of SEQ ID NO: 3 in the Sequence Listing with an arginine residue.

Comparative Examples

It is known that introduction of mutations for improving the heat resistance of an enzyme usually largely decreases the initial rate of reaction, or completely inactivates the enzyme. Also in this application, it was observed that obtained mutants exhibited a decreased initial rate of reaction in most cases although the heat resistance thereof was improved. One example thereof is given in Table 10, in which WT represents wild type and MT represents a mutant.

These mutants were produced using the technique described in step (2) in Example 2.

MT1 was obtained using the plasmid YEp-GAPDHp-GAs-TVX as a template and using the sequences of SEQ ID NO: 43 and SEQ ID NO 44, the sequences of SEQ ID NO: 45 and SEQ ID NO 46, and the sequences of SEQ ID NO: 47 and SEQ ID NO 48, which are given in Table 11 below, as primers.

MT2 was obtained using the plasmid YEp-GAPDHp-GAs-TVX as a template and using the sequences of SEQ ID NO: 7 and SEQ ID NO 8, the sequences of SEQ ID NO: 47 and SEQ ID NO 48, and the sequences of SEQ ID NO: 49 and SEQ ID NO 50, which are given in Table 11 below, as primers.

MT3 was obtained using the plasmid YEp-GAPDHp-GAs-ACX as a template and using the sequences of SEQ ID NO: 51 and SEQ ID NO 52 and the sequences of SEQ ID NO: 53 and SEQ ID NO 54, which are given in Table 11 below, as primers.

The mutation sites of MT1 in Table 10 indicate that, in the amino acid sequence of SEQ ID NO: 1 in the Sequence Listing, a phenylalanine residue is substituted for a tyrosine residue at position 13 (Tyr13Phe), a cysteine residue is substituted for a glycine residue at position 47 (Gly47Cys), and a serine residue is substituted for an asparagine residue at position 151 (Asn151Ser).

The mutation sites of MT2 indicate that, in the amino acid sequence of SEQ ID NO: 1 in the Sequence Listing, an isoleucine residue is substituted for a valine residue at position 46 (Val46Ile), an arginine residue is substituted for a lysine residue at position 58 (Lys58Arg), and a serine residue is substituted for an asparagine residue at position 151 (Asn151Ser).

The mutation sites of MT3 indicate that, in the amino acid sequence of SEQ ID NO: 2 in the Sequence Listing, a cysteine residue is substituted for a serine residue at position 100 (Ser100Cys), and a cysteine residue is substituted for an asparagine residue at position 144 (Asn144Cys).

TABLE 10

| Name of Xylanase | Mutation Sites | Residual Activity (Relative to That Before Heat Treatment) After 16 hours | Initial Rate of Reaction Before Heat Treatment (Relative to WT) Before Heat Treatment |
|---|---|---|---|
| WT (*T. viride*) | — | 5% | 1.00 |
| MT1 (*T. viride*) | Tyr13Phe + Gly47Cys + Asn151Ser | 69% | 0.38 |
| MT2 (*T. viride*) | Val46Ile + Lys58Arg + Asn151Ser | 39% | 0.33 |
| WT (*A. Cellulolyticus*) | — | 63% | 1.00 |
| MT3 (*A. Cellulolyticus*) | Ser100Cys + Asn144Cys | 84% | 0.25 |

TABLE 11

| SEQ ID NO: 43 | CAACAACGGCTTCTTCTACTCGTACTG |
|---|---|
| SEQ ID NO: 44 | CGAGTAGAAGAAGCCGTTGTTGAAGCC |
| SEQ ID NO: 45 | CAACTTTGTCTGCGGCAAGGGATGG |
| SEQ ID NO: 46 | CCATCCCTTGCCGCAGACAAAGTTG |
| SEQ ID NO: 47 | CTCCGTCAGCACGGCGAACCAC |
| SEQ ID NO: 48 | GTGGTTCGCCGTGCTGACGGAG |
| SEQ ID NO: 49 | GCAACTTTATCGGCGGCAAGGGATG |
| SEQ ID NO: 50 | CTTGCCGCCGATAAAGTTGCCCGAG |
| SEQ ID NO: 51 | CACTGTGACGTGCGACGGCGGCAC |
| SEQ ID NO: 52 | CCGCCGTCGCACGTCACAGTGCC |
| SEQ ID NO: 53 | CCGTGCAGTGCCACTTCAATGCC |
| SEQ ID NO: 54 | CATTGAAGTGGCACTGCACGGTAAC |

Example 3

Mass Production of TVX01 and ACX02 Using *T. viride* as Host (1) Mass Production of TVX01 Using *T. viride*
(a) Construction of Plasmid TVX01-pCB1

Using the base sequence encoding the mutant xylanase TVX01 obtained in Example 2 as a template, the DNA sequence of the xylanase portion was obtained by PCR. The primers used in the PCR were presented as SEQ ID NO: 67 and SEQ ID NO 68 in Table 12 below.

Using the full length of the *T. viride*-derived xylanase gene obtained in step (1)(d) in Example 2 as a template, the DNA sequence of the signal portion was obtained by PCR. The primers used in the PCR are presented as SEQ ID NO: 69 and SEQ ID NO 70 in Table 12 below.

The DNA sequence of the signal sequence portion and the DNA sequence of the xylanase portion were linked together using a PCR method, to obtain a sequence that includes StuI site in a sequence upstream of the start codon of the signal sequence portion and XhoI site in a sequence downstream of the stop codon.

The primers used in the PCR are presented as SEQ ID NO: 71 and SEQ ID NO 72 in Table 12 below. The amplified 0.7 kbp DNA fragment was inserted into an expression vector pCR2.1-TOPO using a TOPO TA CLONING KIT (manufactured by Invitrogen Co., Ltd.) according to the protocol attached to the kit, as a result of which a plasmid TOPO-TVX01 was obtained.

TABLE 12

| | |
|---|---|
| SEQ ID NO: 67 | CAGACGATTGGTCCCGGCACGGGCTTCAACAACGGCTACT |
| SEQ ID NO: 68 | CCCCTCGAGTTAGCTGACGGTAATAGAAGCAGAGC |
| SEQ ID NO: 69 | GGGAGGCCTGCGCATCATGGTTTCCTTCACCTCCC |
| SEQ ID NO: 70 | GTGCCGGGACCAATCGTCTGGCGCTTTTCAACGTCCACGG |
| SEQ ID NO: 71 | GGGAGGCCTGCGCATCATGGTTTCCTTCACCTCCC |
| SEQ ID NO: 72 | CCCCTCGAGTTAGCTGACGGTAATAGAAGCAGAGC |

The plasmid TOPO-TVX01 was cleaved with StuI and XhoI, to obtain a gene fragment TVX01-N having about 0.7 kbp. Separately, the pCB1-Eg3X-hphless (WO 2011/021616 pamphlet) was cleaved with StuI and XhoI, and a fragment having a length of about 7 kbp was recovered. The recovered fragment was linked to the gene fragment TVX01-N having a length of about 0.7 kbp using a DNA ligase (manufactured by Takara Shuzo Co., Ltd.), to produce a plasmid TVX01-pCB1. In regard to the reaction conditions for the enzyme and the like, the conditions specified in the instruction manual attached to the kit were adopted. The plasmid TVX01-pCB1 was constructed so as to express TVX01 using its own start codon in the host *T. viride*.

(b) Production of Transformant of *T. viride* Using Plasmid TVX01-pCB1

Transformation of *T. viride* with the plasmid TVX01-pCB1 obtained in step (1)(a) in Example 3 was carried out according to the method disclosed in WO 2011/021616 pamphlet. The transformation was carried out according to a co-transformation method using *T. viride* strain 2, which is a strain lacking uracil biosynthesis gene (pyr4), as a host and a pyr4 gene of *Neurospora crassa* as a selection marker. The *T. viride* strain 2 can be obtained according to a method disclosed in paragraph number [0102] of the specification of Japanese Patent No. 4644603. Specifically, as described in paragraph [0102] of the specification of Japanese Patent No. 4644603, a spore suspension of the *Trichoderma viride* MC300-1 strain (FERM BP-6047) at about $10^9$ CFU/ml was irradiated, while gently shaking, with radiation emitted from two UV lamps disposed at a height of 30 cm. The spore suspension after the UV irradiation was applied to a selection medium, and cultured for 7 days at 28° C. A strain that grew was selected, thereby obtaining *T. viride* strain 2 as a uracil-requiring strain of *Trichoderma viride*. The selection medium had a composition of a minimum medium [0.2% potassium dihydrogen phosphate, 0.4% ammonium sulfate, 0.03% urea, 0.03% magnesium sulfate heptahydrate, 0.03% calcium chloride, 0.5% glucose, 2.5% agar, and 0.01% trace elements (prepared by dissolving 5 mg iron sulfate heptahydrate, 1.56 mg manganese sulfate heptahydrate, 1.4 mg zinc sulfate heptahydrate, and 2 mg cobalt chloride in 1 L of water)] supplemented with 10 μg/mL uridine and 1 mg/mL 5-fluoroorotic acid.

The *T. viride* strain 2 was suspended in a protoplast-forming enzyme solution (1 mg/mL β-glucuronidase, 0.3 mg/mL chitinase, 0.3 mg/mL ZYMOLYASE, and 0.5 mol/L sucrose), to provide protoplasts of the mycelia. The obtained suspension was filtered and centrifuged, and thereafter washed with a SUTC buffer solution (0.5 mol/L sucrose, 10 mmol/L calcium chloride, and 10 mmol/L Tris-HCl (pH: 7.5)).

The protoplasts were suspended in 100 μL of a SUTC buffer solution, and then a DNA solution in an amount of 10 μL that contained 10 μg of the plasmid TVX01-pCB1 and a DNA solution in an amount of 10 μL that contained the pyr4 gene were added thereto. The resultant mixture was allowed to stand still in ice for 5 minutes. Next, 400 μL of a PEG solution (containing PEG4000 at 60%, 10 mmol/L calcium chloride, and 10 mmol/L Tris-HCl (pH: 7.5)) was added thereto, and allowed to stand still in ice for 20 minutes. Then, a SUTC buffer solution in an amount of 10 mL was added thereto, and the resultant mixture was centrifuged. The protoplasts collected were suspended in 1 mL SUTC buffer solution, and 200 μL portions thereof were individually overlaid, together with soft agar, on a minimum medium that contained 0.5 mol/L sucrose. After cultivation at 28° C. for 5 days, colonies that grew were inoculated again into a minimum medium, and the colonies formed therein were used as transformants.

(c) Cultivation and Identification of Transformant Transformed with TVX01-pCB1

The strains that grew in the minimum medium after the introduction of the plasmid TVX01-pCB1 were selected, and cultured according to a method disclosed in WO 98/11239. The obtained culture solution was centrifuged to separate culture supernatant from the microbial cells, and the culture supernatant was allowed to pass through a filter (pore size: 0.2 μm) for filtration and sterilization, thereby preparing a culture supernatant solution. The prepared culture supernatant solution was separated by electrophoresis using 12% Gel SDS-PAGE mini (manufactured by TEFKO Co., Ltd.), and a culture supernatant from which a band of TVX01 was detected well was selected. The selected culture supernatant solution was named mass production TVX01.

(2) Mass Production of ACX02 Using *T. viride*

(a) Modification of ACX02 Gene Codon Suitable for Expression in *T. viride*

In order to enable ACX02 gene to be strongly expressed as an active protein in *T. viride*, a DNA was produced which had changes in bases at 24 positions in total in the signal sequence of *A. cellulolyticus* and ACX02 gene. In Table 13, the base positions for the sequence name ACX02 refers to the base positions in a wild-type *A. cellulolyticus* xylanase gene, which is presented as SEQ ID NO: 4. The base positions for the sequence name *A. cellulolyticus* signal sequence refers to the base positions in SEQ ID NO: 73.

TABLE 13

| Sequence Name | Base Position | Before Modification | After Modification |
|---|---|---|---|
| *A. Cellulolyticus* Signal Sequence | 12 | A | C |
| | 42 | G | T |
| | 66 | A | C |
| | 90 | G | C |

TABLE 13-continued

| Sequence Name | Base Position | Before Modification | After Modification |
|---|---|---|---|
| ACX02 | 37 | A | T |
|  | 38 | G | C |
|  | 39 | T | C |
|  | 78 | T | A |
|  | 81 | T | C |
|  | 106 | A | C |
|  | 108 | G | C |
|  | 138 | A | C |
|  | 279 | A | C |
|  | 312 | A | C |
|  | 405 | G | C |
|  | 474 | A | C |
|  | 495 | A | C |
|  | 552 | T | C |
|  | 573 | A | C |
|  | 648 | G | A |
|  | 663 | C | G |
|  | 718 | A | T |
|  | 719 | G | C |
|  | 720 | T | C |

This modified ACX02 gene was a gene that was designed in consideration of the distribution of the use frequencies of codons in *T. viride*. This modified ACX02 gene was artificially synthesized by Gene Design, Inc. In the artificial synthesis, design was performed such that EcoRI and StuI were included in the sequence upstream of the start codon and such that XhoI and HindIII were included in the downstream of the stop codon. As a result, a plasmid pACX02, in which the codon-modified ACX02 gene was inserted at EcoRI/HindIII of pUC19, was obtained.

(b) Construction of Plasmid ACX02-pCB1

The plasmid pACX02 was cleaved with StuI and XhoI, to obtain a gene fragment ACX02-N having a length of about 850 bp. Separately, the pCB1-Eg3X-hphless (WO 2011/021616 pamphlet) was cleaved with StuI and XhoI, and a fragment having a length of about 7 kbp was recovered. The recovered fragment was ligated to the gene fragment ACX02-N having a length of about 850 bp using a DNA ligase (Takara Shuzo Co., Ltd.), to produce a plasmid ACX02-pCB1. The reaction conditions for the enzyme and the like were set to the conditions specified in the instruction manual attached to the kit. The plasmid ACX02-pCB1 had a configuration such that ACX02 would be expressed in the host *Trichoderma viride* using its own start codon.

(c) Production of Transformant of *Trichoderma viride* Transformed with Plasmid ACX02-pCB1

Transformation of *Trichoderma viride* with the plasmid ACX02-pCB1 obtained in step (2)(b) in Example 3 was carried out according to the method disclosed in WO 2011/021616 pamphlet. The transformation was carried out according to a co-transformation method using *T. viride* strain 2, which is strain lacking uracil biosynthesis gene (pyr4), as a host and a pyr4 gene of *Neurospora crassa* as a selection marker. The *Trichoderma viride* strain 2 was suspended in a protoplast-forming enzyme solution (1 mg/mL of β-glucuronidase, 0.3 mg/mL of chitinase, 0.3 mg/mL of Zymolyase, and 0.5 mol/L of sucrose), to provide protoplasts of the mycelia. This suspension was filtered and centrifuged, and thereafter washed with a SUTC buffer solution (0.5 mol/L sucrose, 10 mmol/L calcium chloride, and 10 mmol/L Tris-HCl (pH: 7.5)).

The protoplasts were suspended in 100 μL of a SUTC buffer solution, and then a DNA solution in an amount of 10 μL that contained 10 μg of the plasmid ACX02-pCB1 and a DNA solution in an amount of 10 μL that contained the pyr4 gene were added thereto. The resultant mixture was allowed to stand still in ice for 5 minutes. Next, 400 μL of a PEG solution (containing PEG4000 at 60%, 10 mmol/L calcium chloride, and 10 mmol/L Tris-HCl (pH: 7.5)) was added thereto, and allowed to stand still in ice for 20 minutes. Then, a SUTC buffer solution in an amount of 10 mL was added thereto, and the resultant mixture was centrifuged. The protoplasts collected were suspended in 1 mL SUTC buffer solution, and 200 μL portions thereof were individually overlaid, together with soft agar, on a minimum medium that contained 0.5 mol/L sucrose. After cultivation at 28° C. for 5 days, colonies that grew were inoculated again into a minimum medium, and the colonies formed therein were used as transformants.

(d) Culturing and Identification of Transformant Transformed with ACX02-pCB1

The strains that grew in the minimum medium after the introduction of the plasmid ACX02-pCB1 were selected, and cultured according to a method disclosed in WO 98/11239.

The obtained culture solution was centrifuged to separate culture supernatant from the microbial cells, and the culture supernatant was allowed to pass through a filter (pore size: 0.2 μm) for filtration and sterilization, thereby preparing a culture supernatant solution. The prepared culture supernatant solution was subjected to SDS-PAGE, and a culture supernatant from which a band of ACX02 was detected well was selected. The selected culture supernatant solution was named mass production ACX02.

Example 4

Transition of Stability of TVX01 Along with Changes in Temperature and pH

The following experiment was conducted using the TVX01 mass-produced by the method employed in Example 3. A 200 mM buffer solution (specified below) and xylanase were mixed together in a ratio of 1:1, and the mixture was treated for a predetermined period of time at various temperatures, and then allowed to stand still in an ice bath for 5 minutes. Then, residual activity was measured according to the method employed in Example 1. The buffer solutions used in this process were a sodium citrate buffer solution (pH: 4.5), a Tris-HCl buffer solution (pH: from 8 to 9), and a sodium glycine buffer solution (pH: 10).

The TVX01 retained an activity of 86% even after heat treatment at pH 4.5 and 50° C. for 72 hours. In addition, TVX01 retained an activity of 68% even after heat treatment at pH 5.5 (the pH of the mutant xylanase stock solution) and at a higher temperature, 70° C., for 5 minutes. Both conditions are conditions in which wild type would completely lose its activity; in contrast, the mutant exhibited improved residual activity under the acidic, high-temperature conditions.

After heat treatment at 50° C. and a pH of from 8 to 10 for 60 minutes, the residual activity of the wild type was 28% at pH 8, was 8% at pH 9, and complete inactivation was observed at pH 10, whereas the residual activity of the mutant was 83% at pH 8, was 60% at pH 9, and was 56% even at pH 10. Furthermore, even after heat treatment at 60° C. for 60 minutes, in which the wild type completely lose its activity, the mutant xylanase retained an activity of 30% at pH 8, an activity of 17% at pH 9, and an activity of 10% at pH 10, which demonstrates that the mutant xylanase exhibits an improved residual activity also under the basic, high-temperature conditions.

As described above, TVX01 according to the invention exhibited a significant improvement in residual activity under conditions where the wild-type enzyme significantly inactivates, such as pH 4.5 or pH of from 8 to 10 with a temperature of from 50° C. to 70° C.

Example 5

Change of Stability of ACX02 Due to Changes in Temperature and pH

An experiment was carried out in the same manner as in Example 4, but using the ACX02 mass-produced by the method employed in Example 3.

The mass-produced ACX02 retained an activity of 84% even after heat treatment at pH 4.5 and 50° C. for 72 hours. A wild-type xylanase treated in the same manner retained an activity that was as low as 45%. Thus, it is demonstrated that the mutant xylanase exhibits an improved residual activity under the acidic, high-temperature conditions, as compared to the wild-type xylanase.

The wild type completely lost its activity after heat treatment at 50° C. and pH of from 8 to 10 for 60 minutes, whereas ACX02 retained an activity of 34% at pH of 8, an activity of 5% at pH 9, and an activity of 2% even at pH 10, which demonstrates that ACX02 retains improved residual activity even under the basic, high-temperature conditions.

As described above, ACX02 according to the invention exhibited a significant improvement in residual activity under conditions where the wild-type enzyme significantly inactivates, such as pH 4.5 or pH of from 8 to 10 with a temperature 50° C.

Example 6

Saccharification Reaction (1) of Lignocellulosic Raw Material

Leaf bleached kraft pulp (LBKP) having a dry weight of 2 g was placed in Erlenmeyer flasks. Then, a cellulase aqueous solution that contained the ACX02 mass-produced by the method of Example 3, a cellulase aqueous solution that contained the TVX01 mass-produced by the method of Example 3, a cellulase aqueous solution that contained a *T. viride*-derived wild-type xylanase as an experimental control, and a cellulase aqueous solution that contained an *A. cellulolyticus*-derived wild-type xylanase as an experimental control were individually added into their respective Erlenmeyer flasks, such that the amount of each cellulase aqueous solution added was 52 mg in terms of protein weight. Then, 20 mM sodium citrate buffer solution (pH 4.5) was added into each Erlenmeyer flask, to prepare a reaction solution in an amount of 20 g. Each of the Erlenmeyer flasks was sealed with a silicone plug. After that, the reaction solution was gently stirred at 50° C., and a saccharification reaction was allowed to proceed. The results are given in Table 14, in which WT. represents the wild-type xylanase.

TABLE 14

| No. | Name of Xylanase | Residual Activity [%] |
|---|---|---|
| (m) | WT (*T. viride*) | 27 |
| (n) | TVX01 | 90 |
| (o) | WT (*A. Cellulolyticus*) | 35 |
| (p) | ACX02 | 90 |

After 72 hours, the wild-type xylanases derived from *A. cellulolyticus* and *T. viride* exhibited residual activities that had decreased to about 30% (rows (m) and (o) in Table 14); in contrast, the mass-produced ACX02 and the mass-produced TVX01 exhibited residual activities of 90% or higher (rows (n) and (p) in Table 14).

Example 7

Saccharification Reaction (2) of Lignocellulosic Raw Material (1) Saccharification Reaction Leaf bleached kraft pulp (LBKP) having a dry weight of 40 g was placed in separable flasks. Then, a cellulase aqueous solution that contained TVX01 mass-produced by the method of Example 3 and a cellulase aqueous solution that contained the ACX02 mass-produced by the method of Example 3 were individually added, in an amount of 347 mg in terms of protein weight, into their respective separable flasks. Then, 20 mM sodium citrate buffer solution (pH 4.5) was added into each separable flask, to prepare a reaction solution in an amount of 400 g. After that, the reaction solution was gently stirred at 50° C., and a saccharification reaction was allowed to proceed. The amount of monosaccharide produced after the reaction was carried out for 72 hours was analyzed by HPLC.

<HPLC Analysis Conditions>
Analyzer: HPLC available from JASCO Corporation
Column: ULTRON PS-80H (300×8 mm; manufactured by Shinwa Chemical Co., Ltd.)
Analysis temperature: 50° C.
Mobile phase: Perchloric acid aqueous solution at pH 2.1

(2) Recovery of Enzyme

The saccharification reaction solution (the reaction solution after 72 hours of reaction) was centrifuged at 7000×g, and the precipitate was recovered. The remaining centrifugal supernatant solution was treated with a commercially available UF membrane (product name: Microza UF Pencil Module AIP-0013D manufactured by Asahi Kasei Chemicals Corporation), to obtain a concentrated fraction.

(3) Re-Saccharification Reaction Using Recovered Enzyme

The precipitate obtained by the 7000×g centrifugation of the saccharification reaction solution and the concentrated fraction obtained by the treatment with the UF membrane were placed in a separable flask. Next, leaf bleached kraft pulp (LBKP) was added thereto in an amount of 40 g in terms of final solid content, and the resultant mixture was gently stirred at 50° C. and a saccharification reaction was allowed to proceed. Then, the amount of monosaccharide produced after 72 hours of reaction was analyzed by HPLC.

(4) Results of Saccharification Reaction

After 72 hours from the start of the first reaction (the number of times of enzyme reutilization: zero times), the concentration of glucose and xylose accumulated in the saccharification reaction solution that contained TVX01 was 79.1 g/L, in which the concentration of glucose accumulated in the saccharification reaction solution was 65.1 g/L. The concentration of glucose and xylose accumulated in the saccharification reaction solution that contained the wild-type *T. viride*-derived xylanase was 78.0 g/L, in which the concentration of glucose accumulated in the saccharification reaction solution was 64.7 g/L. In the saccharification reaction solution that contained ACX02, the concentration of glucose and xylose accumulated was 61.3 g/L, in which the concentration of glucose accumulated was 49.9 g/L. The enzymes contained in these saccharification reaction solutions were re-utilized for saccharification reactions by the method described above.

The concentration of glucose and xylose accumulated in the first cycle of reutilization was 70.7 g/L in the saccharification reaction solution that contained TVX01, 53.3 g/L in the saccharification reaction solution that contained the wild-type *T. viride*-derived xylanase, and 53.1 g/L in the saccharification reaction solution that contained ACX02.

The concentration of glucose accumulated in the first cycle of reutilization was 58.7 g/L in the saccharification reaction solution that contained TVX01, 45.0 g/L in the saccharification reaction solution that contained the wild-type *T. viride*-derived xylanase, and 43.5 g/L in the saccharification reaction solution that contained ACX02.

The concentration of glucose and xylose accumulated in the second cycle of reutilization was 63.6 g/L in the saccharification reaction solution that contained TVX01, 42.3 g/L in the saccharification reaction solution that contained the wild-type *T. viride*-derived xylanase, and 42.6 g/L in the saccharification reaction solution that contained ACX02.

The concentration of glucose accumulated in the second cycle of reutilization was 53.0 g/L in the saccharification reaction solution that contained TVX01, 35.8 g/L in the saccharification reaction solution that contained the wild-type *T. viride*-derived xylanase, and 34.6 g/L in the saccharification reaction solution that contained ACX02.

The obtained results are given as relative values assuming that the concentration of accumulated sugars in the 0th cycle of reutilization is 100%. The results are given in Tables 15 and 16, in which WT. represents wild-type xylanase.

TABLE 15

| No. | Name of Xylanase | Concentration of Glucose and Xylose Accumulated (Relative Values) | | |
|---|---|---|---|---|
| | | 0th Cycle | 1st Cycle | 2nd Cycle |
| (m) | WT (*T. viride*) | 100 | 68 | 54 |
| (n) | TVX01 | 100 | 89 | 80 |
| (p) | ACX02 | 100 | 87 | 70 |

TABLE 16

| No. | Name of Xylanase | Concentration of Glucose Accumulated (Relative Values) | | |
|---|---|---|---|---|
| | | 0th Cycle | 1st Cycle | 2nd Cycle |
| (m) | WT (*T. viride*) | 100 | 70 | 55 |
| (n) | TVX01 | 100 | 90 | 81 |
| (p) | ACX02 | 100 | 87 | 69 |

As demonstrated in Table 15, it was clarified that the mutant xylanases TVX01 and ACX02 according to the invention are highly suitable for used in the saccharification reaction in which reutilization of enzymes is carried out.

As demonstrated in Table 16, it was clarified that not only the efficiency of production of xylose but also the efficiency of production of glucose is increased by using the mutant xylanase according to the invention.

Besides, effects similar to the above were obtained also in cases in which TVX01 and ACX02 according to the invention were used with needle bleached kraft pulp (NBKP).

Example 8

Method of Bleaching Pulp (1) Treatment of Pulp with Xylanase

A commercially available milk carton is used as a pulp. The raw material of milk cartons is timber from thinned softwood, remnant wood generated by lumbering, or the like, and is a virgin pulp that contains lignin, which is a coloring component.

A well-washed milk carton is cut into about 5-cm square pieces, and immersed in water for a length of time of from about 2 days to about 5 days. Thereafter, a polyethylene film on the surface thereof is removed.

Water in which the paper pieces have been immersed is heated to 50° C., and the mutant xylanase TVX01 according to the invention and the mutant xylanase ACX02 according to the invention are individually added thereto. The same treatment is carried out, but using their respective wild-type xylanases as controls for comparison. Each of the xylanases used in this example are derived from a filamentous fungus. The amount of xylanase to be added is controlled so as to provide an optimal mixing ratio. In addition, the treatment time is also controlled so as to provide an optimum treatment time. Moreover, a sample that would not be treated with xylanase is also prepared.

After that, a commercially available chlorine-containing bleaching agent is added, and the paper pieces are allowed to stand still for half a day at a pH of from 7 to 10. The paper pieces are washed well with water, and torn into small pieces, and stirred with an appropriate amount of water in a household mixer until the paper pieces become unable to be seen.

The fibers are processed into paper using a commercially available papermaking apparatus, and then water is removed therefrom, and the paper is dried.

(2) Measurement of Whiteness

Whiteness (JIS Z 8715) of the paper produced as described above is measured using a UV-visible spectral whiteness meter.

(3) In cases in which the mutant xylanase TVX01 according to the invention and the mutant xylanase ACX02 according to the invention are added, pulp can be bleached even under the conditions of pH 7 to pH 10.

Example 9

Detergent (1) Cleaning of Fluffed Fabric

Old fluffed fabric is used as a material to be washed. The detergent to be used is prepared by adding the mutant xylanase TVX01 according to the invention or the mutant xylanase ACX02 according to the invention to a commercially available detergent. Treatment is performed in the same manner as above, but using their respective wild-type xylanases as controls for comparison. Each of the xylanases used in this example is derived from a filamentous fungus. In addition, old fluffed fabric not treated with xylanase is also prepared. The amount of xylanase to be added is controlled so as to provide an optimal mixing ratio. Timing of the addition thereof is set to be simultaneous with the addition of the detergent.

800 ml of water is added into a 1 L separable flask, and the detergent and the xylanase are added thereto. Washing is conducted at 50° C. and a pH of from 7 to 10 for 1 hour while rotating the separable flask at 60 rpm. Thereafter, natural drying is performed.

(2) Measurement of Degree of Removal of Fluff

The state of removal of fluff is observed under a stereomicroscope. In addition, the degree of removal of fluff in the fabric after washing is measured using a spectrophotometer.

(3) In cases in which the mutant xylanase TVX01 according to the invention and the mutant xylanase ACX02 according to the invention are added, fluffing is suppressed under the conditions of a pH of from 7 to 10 and a temperature of 50° C.

Example 10

Animal Feed (1) Production of Animal Feed

The mutant xylanase TVX01 according to the invention or the mutant xylanase ACX02 according to the invention is added to a powdery feed for experimental animals. Treatment is performed in the same manner but using their respective wild-type xylanases as controls for comparison. Each of the xylanases used in this example is derived from a filamentous fungus. In addition, powdery feed not treated with xylanase is also prepared. The amount of xylanase to be added is controlled so as to provide an optimal mixing ratio, and the mixture is pelletized.

(2) Measurement of Degree of Cell Wall Decomposition in Shaped Animal Feed

After the shaped animal feed is allowed to stand still overnight, the animal feed is sliced with a commercially available razor and subjected to Gram staining on the prepared slide, and the degree of coloring of the cell wall is observed under an optical microscope. In addition, the animal feed that has been allowed to stand still overnight is vigorously mixed with 100 mM sodium citrate buffer solution (pH 4.5), and centrifuged at 5000×g for 15 minutes. Then, the supernatant is removed, and the amount of reducing sugar in the supernatant is measured using the DNS method (Bailey et. al, 1992).

Example 11

Bread-Making Modifier (1) Bread Making

Bread is made using the straight dough method. The formulation of ingredients is given in Table 17 below. For all of the ingredients, commercially available materials for home use are used.

TABLE 17

| Name of Ingredient | Amount Added (g) |
| --- | --- |
| Hard flour | 320 |
| Milk | 100 |
| Butter | 25 |
| Dry Yeast | 4 |
| Salt | 5 |
| Sugar | 20 |

The mutant xylanase TVX01 according to the invention or the mutant xylanase ACX02 according to the invention is added as a bread-making modifier. Treatment is performed in the same manner but using their respective wild-type xylanases as controls for comparison.

The timing of addition thereof is set to be simultaneous with the mixing of ingredients. The amount of xylanase is controlled so as to provide an optimum mixing ratio. In addition, dough not treated with xylanase is also prepared.

The dough obtained was allowed to ferment at about 37° C. for a length of time of from about 1 hour to about 2 hours until the size thereof increased to about twice the original size, and then baked in a microwave.

(2) Observation of Particle Structure of Bread

The baked bread is sliced with a commercially available razor, and the particle structure is observed under a stereo-microscope.

(3) Measurement of Loaf Volume

The baked bread is allowed to stand still overnight, and then the loaf volume of the baked bread is measured using a rapeseed displacement method.

(4) In cases in which the mutant xylanase TVX01 according to the invention and the mutant xylanase ACX02 according to the invention are added, the mutant xylanases are capable of stable reaction under the conditions of from 35° C. to 40° C. for from 1 to 2 hours in the fermentation process.

The disclosure of Japanese Patent Application Nos. 2011-257389, filed Nov. 25, 2011, and the disclosure of Japanese Patent Application No. 2012-099096, filed Apr. 24, 2012, are incorporated herein by reference in their entireties.

All publications, patent applications, and technical standards mentioned in this specification are herein incorporated by reference to the same extent as if each individual publication, patent application, or technical standard was specifically and individually indicated to be incorporated by reference.

The invention claimed is:

1. A nucleic acid encoding a mutant xylanase, the mutant xylanase comprising the following amino acid residues substitutions in the amino acid sequence of SEQ ID NO: 1:
   a leucine residue substituted for an asparagine residue at position 29;
   an arginine residue substituted for a lysine residue at position 58;
   an amino acid residue, other than a tyrosine residue, substituted for a tyrosine residue at position 27; and
   an amino acid residue, other than an asparagine residue, substituted for an asparagine residue at position 44, or
   the mutant xylanase comprising 1 to 10 amino acid residues substitution in the amino acid sequence of SEQ ID NO: 1 in addition of the following amino acid residues substitutions:
   a leucine residue substituted for an asparagine residue at position 29,
   an arginine residue substituted for a lysine residue at position 58,
   a phenylalanine residue substituted for a tyrosine residue at position 27, and
   a serine residue substituted for an asparagine residue at position 44.

2. The nucleic acid according to claim 1, wherein the amino acid residue, other than a tyrosine residue, substituted for the tyrosine residue at position 27 in the amino acid sequence of SEQ ID NO: 1 is a phenylalanine residue, and the amino acid residue, other than an asparagine residue, substituted for an asparagine residue at position 44 in the amino acid sequence of SEQ ID NO: 1 is a serine residue.

3. An expression vector comprising the nucleic acid according to claim 1.

4. A transformant comprising the expression vector according to claim 3.

5. The transformant according to claim 4, wherein a host cell of the transformant is a cell obtained from *Escherichia coli, Bacillus subtilis*, yeast, an actinomycete, or a filamentous fungus.

6. The transformant according to claim 5, wherein the filamentous fungus belongs to the genus *Trichoderma*, the genus *Acremonium*, the genus *Humicola*, or the genus *Aspergillus*.

7. The transformant according to claim 5, wherein the filamentous fungus is *Trichoderma viride, Acremonium cellulolyticus, Humicola insolens*, or *Aspergillus niger*.

8. A method of producing a mutant xylanase, the method comprising culturing the transformant according to claim 4 and recovering the mutant xylanase from at least one of the cultured transformant or a culture product of the transformant.

* * * * *

SEQUENCE LISTING

```
<160> NUMBER OF SEQ ID NOS: 75

<210> SEQ ID NO 1
<211> LENGTH: 190
<212> TYPE: PRT
<213> ORGANISM: Trichoderma viride

<400> SEQUENCE: 1

Gln Thr Ile Gly Pro Gly Thr Gly Phe Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
```

```
                50                  55                  60
Thr Tyr Asn Pro Asn Gly Asn Ser Tyr Leu Ser Val Tyr Gly Trp Ser
 65                  70                  75                  80

Arg Asn Pro Leu Ile Glu Tyr Ile Val Glu Asn Phe Gly Thr Tyr
                     85                  90                  95

Asn Pro Ser Thr Gly Ala Thr Lys Leu Gly Glu Val Thr Ser Asp Gly
                100                 105                 110

Ser Val Tyr Asp Ile Tyr Arg Thr Gln Arg Val Asn Gln Pro Ser Ile
            115                 120                 125

Glu Gly Thr Ser Thr Phe Tyr Gln Tyr Trp Ser Val Arg Arg Thr His
            130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190

<210> SEQ ID NO 2
<211> LENGTH: 243
<212> TYPE: PRT
<213> ORGANISM: Acremonium cellulolyticus

<400> SEQUENCE: 2

Ala Glu Ala Ile Asn Tyr Asn Gln Asn Tyr Ile Ala Ser Gly Ala Asn
 1               5                  10                  15

Val Gln Tyr Ser Pro Asn Ile Ala Ala Gly Ser Phe Ser Ile Asn Tyr
                 20                  25                  30

Asn Thr Gln Gly Asp Phe Val Val Gly Leu Gly Trp Gln Pro Gly Asp
             35                  40                  45

Ala Asn Pro Ile Thr Tyr Ser Gly Ser Phe Ser Ala Ser Gly Val Gly
 50                  55                  60

Ile Leu Ala Val Tyr Gly Trp Thr Thr Asn Pro Leu Val Glu Tyr Tyr
 65                  70                  75                  80

Ile Met Glu Val His Asp Gly Tyr Gln Thr Val Gly Thr His Lys Gly
                 85                  90                  95

Thr Val Thr Ser Asp Gly Gly Thr Tyr Asp Ile Trp Glu His Gln Gln
                100                 105                 110

Val Asn Gln Pro Ser Ile Leu Gly Thr Ser Thr Phe Asn Gln Tyr Ile
            115                 120                 125

Ser Ile Arg Gln Ser Pro Arg Thr Ser Gly Thr Val Thr Val Gln Asn
130                 135                 140

His Phe Asn Ala Trp Ala Gln Ala Gly Leu Asn Leu Gly Thr Met Asn
145                 150                 155                 160

Tyr Gln Val Leu Ala Val Glu Ser Trp Ser Gly Ser Gly Ser Gly Gln
                165                 170                 175

Ile Ser Leu Ser Lys Gly Thr Gly Gly Thr Thr Thr Thr Thr Pro
                180                 185                 190

Thr Gly Pro Thr Ser Thr Ser Thr Ala Pro Ser Ser Gly Gly Thr Gly
            195                 200                 205

Ala Ala Gln Trp Gly Gln Cys Gly Gly Ile Gly Trp Thr Gly Pro Thr
            210                 215                 220

Thr Cys Val Ser Pro Tyr Thr Cys Lys Tyr Phe Asn Ala Tyr Tyr Ser
225                 230                 235                 240
```

Gln Cys Gln

<210> SEQ ID NO 3
<211> LENGTH: 573
<212> TYPE: DNA
<213> ORGANISM: Trichoderma viride

<400> SEQUENCE: 3

```
cagacgattg gtcccggcac gggcttcaac aacggctact tctactcgta ctggaacgac      60
ggccacggcg gcgtgacgta caccaatggc cccggcggcc agttctccgt caactggtcc     120
aactcgggca actttgtcgg cggcaaggga tggcagcccg gcaccaagaa caaggtcatc     180
aacttctcgg gcacctacaa ccccaacggc aacagctacc tctccgtgta cggctggtcg     240
cgcaaccccc tgatcgagta ctacatcgtc gagaactttg gcacctacaa cccgtccacc     300
ggcgccacca agctgggcga ggtgacgtcg gacggcagcg tctacgacat ctaccgcacg     360
cagcgcgtca accagccgtc catcgagggc acctccacct tttaccagta ctggtccgtc     420
cgccgcaccc accgctccag cggctccgtc aacacggcga accacttcaa cgcgtgggcc     480
tcgcacggcc tgacgctggg caccatggat taccagattg ttgccgtgga gggctacttt     540
agctctggct ctgcttctat taccgtcagc taa                                  573
```

<210> SEQ ID NO 4
<211> LENGTH: 732
<212> TYPE: DNA
<213> ORGANISM: Acremonium cellulolyticus

<400> SEQUENCE: 4

```
gctgaggcga tcaactacaa ccaaaactac attgctagtg gtgccaatgt tcaatactcg      60
cccaacatcg ctgcgggttc tttctccatc aactacaata cgcaggggga ctttgtggtg     120
ggacttggtt ggcaaccagg tgatgctaac cccatcacct acagcggctc cttctcggcc     180
tcgggtgttg gtatccttgc cgtgtacggc tggaccacca cccgctcgt ggaatactat      240
atcatggagg ttcacgacgg ataccagact gtcggcacac acaagggcac tgtgacgagc     300
gacggcggca cctatgatat ctgggagcac cagcaggtca atcagccgtc cattctgggc     360
acctccacct tcaaccagta catctcgatc cgccaaagcc cccggacgag cggtacggtt     420
accgtgcaga accacttcaa tgcctgggcg caggcgggct tgaatctcgg cacaatgaac     480
taccaggtcc tggcagtcga gagctggagc ggcagcggct ctggacaaat ctcgctcagc     540
aagggcactg gcggtggcac caccaccacc acacccacgg gtcccaccag cacgagcacc     600
gctccttcga gcggaggtac cggtgctgct caatggggac aatgcggagg aattggctgg     660
accggcccga ctacctgcgt gtccccttat acttgcaagt actttaacgc ttactacagt     720
cagtgccaat ag                                                          732
```

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 5

```
gtacaccctc ggccccggcg gccag                                            25
```

<210> SEQ ID NO 6
<211> LENGTH: 25

```
<212> TYPE: DNA
<213> ORGANISM: Artificial Sequence
<220> FEATURE:
<223> OTHER INFORMATION: Oligonucleotide to act as a PCR primer

<400> SEQUENCE: 6
cggggccgag ggtgtacgtc acgcc                                              25

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 7
caagaacagg gtcatcaact tctcg                                              25

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide to act as a PCR primer

<400> SEQUENCE: 8
gatgaccctg ttcttggtgc cgg                                                23

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 9
cgtgacgttc accctcggcc ccggc                                              25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 10
cgagggtgaa cgtcacgccg ccgtg                                              25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 11
ctcgggcagc tttgtcggcg gcaag                                              25

<210> SEQ ID NO 12
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 12
```

```
cgacaaagct gcccgagttg gaccag                                          26

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 13
catcaactac gatacgcagg gggac                                           25

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 14
ccctgcgtat cgtagttgat ggag                                            24

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 15
gatacgcaga gggactttgt ggtgg                                           25

<210> SEQ ID NO 16
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 16
caaagtccct ctgcgtatcg tagttg                                          26

<210> SEQ ID NO 17
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 17
gataccagtc tgtcggcaca cacaag                                          26

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 18
gccgacagac tggtatccgt cgtg                                            24

<210> SEQ ID NO 19
<211> LENGTH: 24
<212> TYPE: DNA
<213> ORGANISM: Artificial Sequence
```

-continued

```
<220> FEATURE:
<223> OTHER INFORMATION: Oligonucleotide to act as a PCR primer

<400> SEQUENCE: 19
gatccgccga agcccccgga cgag                                          24

<210> SEQ ID NO 20
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 20
gggggcttcg gcggatcgag atgtac                                        26

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide to act as a PCR primer

<400> SEQUENCE: 21
caggcgggca tgaatctcgg cacaatg                                       27

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 22
ccgagattca tgcccgcctg cgccc                                         25

<210> SEQ ID NO 23
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 23
gcagcggcac tggacaaatc tcgctc                                        26

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 24
gatttgtcca gtgccgctgc cgctcc                                        26

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 25
cacgggtcac accagcacga gcac                                          24
```

```
<210> SEQ ID NO 26
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 26
gtgctggtgt gacccgtggg tgtg                                          24

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 27
gtcacaccaa cacgagcacc gctcc                                         25

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 28
gtgctcgtgt tggtgtgacc cgtgg                                         25

<210> SEQ ID NO 29
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 29
caatgcggag aaattggctg gaccgg                                        26

<210> SEQ ID NO 30
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 30
ccagccaatt tctccgcatt gtcccc                                        26

<210> SEQ ID NO 31
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 31
ctttctccgt caactacaat acgc                                          24

<210> SEQ ID NO 32
<211> LENGTH: 23
<212> TYPE: DNA
<213> ORGANISM: Artificial Sequence
<220> FEATURE:
<223> OTHER INFORMATION: Oligonucleotide to act as a PCR primer
```

-continued

<400> SEQUENCE: 32
gtagttgacg gagaaagaac ccg                                    23

<210> SEQ ID NO 33
<211> LENGTH: 28
<212> TYPE: DNA
<213> ORGANISM: Artificial Sequence
<220> FEATURE:
<223> OTHER INFORMATION: Oligonucleotide to act as a PCR primer

<400> SEQUENCE: 33
gtcaactacg atacgcaggg ggactttg                               28

<210> SEQ ID NO 34
<211> LENGTH: 28
<212> TYPE: DNA
<213> ORGANISM: Artificial Sequence
<220> FEATURE:
<223> OTHER INFORMATION: Oligonucleotide to act as a PCR primer

<400> SEQUENCE: 34
ccctgcgtat cgtagttgac ggagaaag                               28

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 35
ctccttcacg gcctcgggtc gggtg                                  25

<210> SEQ ID NO 36
<211> LENGTH: 26
<212> TYPE: DNA
<213> ORGANISM: Artificial Sequence
<220> FEATURE:
<223> OTHER INFORMATION: Oligonucleotide to act as a PCR primer

<400> SEQUENCE: 36
ccgaggccgt gaaggagccg ctgtag                                 26

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 37
cgcttaccac agtcagtgcc aatag                                  25

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide to act as a PCR primer

<400> SEQUENCE: 38
cactgactgt ggtaagcgtt aaagtac                                27

<210> SEQ ID NO 39

```
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 39
cagtcagagc caatagggat cctc                                              24

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 40
cctattggct ctgactgtag taagc                                             25

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 41
cgtgacgttc accaatggcc ccggc                                             25

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 42
cattggtgaa cgtcacgccg ccgtg                                             25

<210> SEQ ID NO 43
<211> LENGTH: 27
<212> TYPE: DNA
<213> ORGANISM: Artificial Sequence
<220> FEATURE:
<223> OTHER INFORMATION: Oligonucleotide to act as a PCR primer

<400> SEQUENCE: 43
caacaacggc ttcttctact cgtactg                                           27

<210> SEQ ID NO 44
<211> LENGTH: 27
<212> TYPE: DNA
<213> ORGANISM: Artificial Sequence
<220> FEATURE:
<223> OTHER INFORMATION: Oligonucleotide to act as a PCR primer

<400> SEQUENCE: 44
cgagtagaag aagccgttgt tgaagcc                                           27

<210> SEQ ID NO 45
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 45
```
caactttgtc tgcggcaagg gatgg                                          25

<210> SEQ ID NO 46
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 46
ccatcccttg ccgcagacaa agttg                                          25

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide to act as a PCR primer

<400> SEQUENCE: 47
ctccgtcagc acggcgaacc ac                                             22

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide to act as a PCR primer

<400> SEQUENCE: 48
gtggttcgcc gtgctgacgg ag                                             22

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 49
gcaactttat cggcggcaag ggatg                                          25

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 50
cttgccgccg ataaagttgc ccgag                                          25

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 51
cactgtgacg tgcgacggcg gcac                                           24

<210> SEQ ID NO 52
<211> LENGTH: 23
<212> TYPE: DNA

```
<213> ORGANISM: Artificial Sequence
<220> FEATURE:
<223> OTHER INFORMATION: Oligonucleotide to act as a PCR primer

<400> SEQUENCE: 52
ccgccgtcgc acgtcacagt gcc                                            23

<210> SEQ ID NO 53
<211> LENGTH: 23
<212> TYPE: DNA
<213> ORGANISM: Artificial Sequence
<220> FEATURE:
<223> OTHER INFORMATION: Oligonucleotide to act as a PCR primer

<400> SEQUENCE: 53
ccgtgcagtg ccacttcaat gcc                                            23

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide to act as a PCR primer

<400> SEQUENCE: 54
cattgaagtg gcactgcacg gtaac                                          25

<210> SEQ ID NO 55
<211> LENGTH: 29
<212> TYPE: DNA
<213> ORGANISM: Artificial Sequence
<220> FEATURE:
<223> OTHER INFORMATION: Oligonucleotide to act as a PCR primer

<400> SEQUENCE: 55
gactagcccg ggtcgagttt atcattatc                                      29

<210> SEQ ID NO 56
<211> LENGTH: 32
<212> TYPE: DNA
<213> ORGANISM: Artificial Sequence
<220> FEATURE:
<223> OTHER INFORMATION: Oligonucleotide to act as a PCR primer

<400> SEQUENCE: 56
gacgagagat ctccattttg tttatttatg tg                                  32

<210> SEQ ID NO 57
<211> LENGTH: 32
<212> TYPE: DNA
<213> ORGANISM: Artificial Sequence
<220> FEATURE:
<223> OTHER INFORMATION: Oligonucleotide to act as a PCR primer

<400> SEQUENCE: 57
gactagagat ctatgcaact gttcaatttg cc                                  32

<210> SEQ ID NO 58
<211> LENGTH: 29
<212> TYPE: DNA
<213> ORGANISM: Artificial Sequence
<220> FEATURE:
<223> OTHER INFORMATION: Oligonucleotide to act as a PCR primer

<400> SEQUENCE: 58
cagcatgagc tcagcagaaa ccagcaaag                                      29
```

<210> SEQ ID NO 59
<211> LENGTH: 30
<212> TYPE: DNA
<213> ORGANISM: Artificial Sequence
<220> FEATURE:
<223> OTHER INFORMATION: Oligonucleotide to act as a PCR primer

<400> SEQUENCE: 59
atggtttcct tcacctccct cctcgccggc                                  30

<210> SEQ ID NO 60
<211> LENGTH: 30
<212> TYPE: DNA
<213> ORGANISM: Artificial Sequence
<220> FEATURE:
<223> OTHER INFORMATION: Oligonucleotide to act as a PCR primer

<400> SEQUENCE: 60
ttagctgacg gtaatagaag cagagccaga                                  30

<210> SEQ ID NO 61
<211> LENGTH: 30
<212> TYPE: DNA
<213> ORGANISM: Artificial Sequence
<220> FEATURE:
<223> OTHER INFORMATION: Oligonucleotide to act as a PCR primer

<400> SEQUENCE: 61
atgggcatct catctattct tctctctgct                                  30

<210> SEQ ID NO 62
<211> LENGTH: 30
<212> TYPE: DNA
<213> ORGANISM: Artificial Sequence
<220> FEATURE:
<223> OTHER INFORMATION: Oligonucleotide to act as a PCR primer

<400> SEQUENCE: 62
ctattggcac tgactgtagt aagcgttaaa                                  30

<210> SEQ ID NO 63
<211> LENGTH: 28
<212> TYPE: DNA
<213> ORGANISM: Artificial Sequence
<220> FEATURE:
<223> OTHER INFORMATION: Oligonucleotide to act as a PCR primer

<400> SEQUENCE: 63
gattaggagc tccagacgat tggtcccg                                    28

<210> SEQ ID NO 64
<211> LENGTH: 29
<212> TYPE: DNA
<213> ORGANISM: Artificial Sequence
<220> FEATURE:
<223> OTHER INFORMATION: Oligonucleotide to act as a PCR primer

<400> SEQUENCE: 64
gactagggat ccttagctga cggtaatag                                   29

<210> SEQ ID NO 65
<211> LENGTH: 30
<212> TYPE: DNA
<213> ORGANISM: Artificial Sequence
<220> FEATURE:

<223> OTHER INFORMATION: Oligonucleotide to act as a PCR primer

<400> SEQUENCE: 65
gattatgagc tcgctgaggc gatcaactac                              30

<210> SEQ ID NO 66
<211> LENGTH: 31
<212> TYPE: DNA
<213> ORGANISM: Artificial Sequence
<220> FEATURE:
<223> OTHER INFORMATION: Oligonucleotide to act as a PCR primer

<400> SEQUENCE: 66
gattagggat ccctattggc actgactgta g                            31

<210> SEQ ID NO 67
<211> LENGTH: 40
<212> TYPE: DNA
<213> ORGANISM: Artificial Sequence
<220> FEATURE:
<223> OTHER INFORMATION: Oligonucleotide to act as a PCR primer

<400> SEQUENCE: 67
cagacgattg gtcccggcac gggcttcaac aacggctact                   40

<210> SEQ ID NO 68
<211> LENGTH: 35
<212> TYPE: DNA
<213> ORGANISM: Artificial Sequence
<220> FEATURE:
<223> OTHER INFORMATION: Oligonucleotide to act as a PCR primer

<400> SEQUENCE: 68
cccctcgagt tagctgacgg taatagaagc agagc                        35

<210> SEQ ID NO 69
<211> LENGTH: 35
<212> TYPE: DNA
<213> ORGANISM: Artificial Sequence
<220> FEATURE:
<223> OTHER INFORMATION: Oligonucleotide to act as a PCR primer

<400> SEQUENCE: 69
gggaggcctg cgcatcatgg tttccttcac ctccc                        35

<210> SEQ ID NO 70
<211> LENGTH: 40
<212> TYPE: DNA
<213> ORGANISM: Artificial Sequence
<220> FEATURE:
<223> OTHER INFORMATION: Oligonucleotide to act as a PCR primer

<400> SEQUENCE: 70
gtgccgggac caatcgtctg gcgcttttca acgtccacgg                   40

<210> SEQ ID NO 71
<211> LENGTH: 35
<212> TYPE: DNA
<213> ORGANISM: Artificial Sequence
<220> FEATURE:
<223> OTHER INFORMATION: Oligonucleotide to act as a PCR primer

<400> SEQUENCE: 71
gggaggcctg cgcatcatgg tttccttcac ctccc                        35

```
<210> SEQ ID NO 72
<211> LENGTH: 35
<212> TYPE: DNA
<213> ORGANISM: Artificial Sequence
<220> FEATURE:
<223> OTHER INFORMATION: Oligonucleotide to act as a PCR primer

<400> SEQUENCE: 72
cccctcgagt tagctgacgg taatagaagc agagc                                35

<210> SEQ ID NO 73
<211> LENGTH: 117
<212> TYPE: DNA
<213> ORGANISM: A. cellulolyticus

<400> SEQUENCE: 73
atgggcatct catctattct tctctctgct ctgatcgcgg ggggagcctt ggctctgccc     60
gctgcagaac ctgtgtcgtt cgatatccgg gatgaaaaca tcaccctggc gcgccgc      117

<210> SEQ ID NO 74
<211> LENGTH: 672
<212> TYPE: DNA
<213> ORGANISM: T. viride

<400> SEQUENCE: 74
atggtttcct tcacctccct cctcgccggc gtcgccgcca tctccggagt cttggccgct    60
cccgctgctg aggtcgagtc cgtggacgtt gaaaagcgcc agacgattgg tcccggcacg   120
ggcttcaaca acggctactt ctactcgtac tggaacgacg ccacggcgg cgtgacgtac    180 accaatggcc ccggcggcca gttctccgtc aactggtcca actcgggcaa ctttgtcggc   240
ggcaagggat ggcagcccgg caccaagaac aaggtcatca acttctcggg cacctacaac   300
cccaacggca acagctacct ctccgtgtac ggctggtcgc gcaaccccct gatcgagtac   360
tacatcgtcg agaactttgg cacctacaac ccgtccaccg gcgccaccaa gctgggcgag   420
gtgacgtcgg acggcagcgt ctacgacatc taccgcacgc agcgcgtcaa ccagccgtcc   480
atcgagggca cctccacctt ttaccagtac tggtccgtcc gccgcaccca ccgctccagc   540
ggctccgtca acacggcgaa ccacttcaac gcgtgggcct cgcacggcct gacgctgggc   600
accatggatt accagattgt tgccgtggag ggctacttta gctctggctc tgcttctatt   660
accgtcagct aa                                                       672

<210> SEQ ID NO 75
<211> LENGTH: 849
<212> TYPE: DNA
<213> ORGANISM: A. cellulolyticus

<400> SEQUENCE: 75
atgggcatct catctattct tctctctgct ctgatcgcgg ggggagcctt ggctctgccc    60
gctgcagaac ctgtgtcgtt cgatatccgg gatgaaaaca tcaccctggc gcgccgcgct  120
gaggcgatca actacaacca aaactacatt gctagtggtg ccaatgttca atactcgccc  180
aacatcgctg cgggttcttt ctccatcaac tacaatacgc aggggggactt tgtggtggga  240 cttggttggc aaccaggtga tgctaacccc atcacctaca cggctccctt ctcggcctcg  300
ggtgttggta tccttgccgt gtacggctgg accaccaacc cgctcgtgga atactatatc  360
atggaggttc acgacggata ccagactgtc ggcacacaca agggcactgt gacgagcgac  420
ggcggcacct atgatatctg ggagcaccag caggtcaatc agccgtccat tctgggcacc   480
```

-continued

```
tccaccttca accagtacat ctcgatccgc caaagccccc ggacgagcgg tacggttacc      540
gtgcagaacc acttcaatgc ctgggcgcag gcgggcttga atctcggcac aatgaactac      600
caggtcctgg cagtcgagag ctggagcggc agcggctctg gacaaatctc gctcagcaag      660
ggcactggcg gtggcaccac caccaccaca cccacgggtc ccaccagcac gagcaccgct      720
ccttcgagcg gaggtaccgg tgctgctcaa tggggacaat gcggaggaat tggctggacc      780
ggcccgacta cctgcgtgtc cccttatact tgcaagtact ttaacgctta ctacagtcag      840
tgccaatag                                                              849
```